(12) United States Patent
Griffis et al.

(10) Patent No.: US 10,820,919 B2
(45) Date of Patent: Nov. 3, 2020

(54) EXTRACORPOREAL SHOCKWAVE LITHOTRIPSY (ESWL) SYSTEM AND METHOD USING IN-SITU SENSING OF SYSTEM AND DEVICE DATA AND THERAPEUTIC/SYSTEM/DEVICE LEVEL CONTROL

(71) Applicant: Translational Technologies, LLC, Tucson, AZ (US)

(72) Inventors: Andrew James Griffis, Tucson, AZ (US); Christopher Mark Gleason, Tucson, AZ (US)

(73) Assignee: TRANSLATIONAL TECHNOLOGIES, LLC, Tucson, AZ (US)

( * ) Notice: Subject to any disclaimer, the term of this patent is extended or adjusted under 35 U.S.C. 154(b) by 288 days.

(21) Appl. No.: 15/845,296

(22) Filed: Dec. 18, 2017

(65) Prior Publication Data
US 2018/0193046 A1  Jul. 12, 2018

Related U.S. Application Data

(60) Provisional application No. 62/443,164, filed on Jan. 6, 2017.

(51) Int. Cl.
*A61B 17/225* (2006.01)
*A61B 34/10* (2016.01)
(Continued)

(52) U.S. Cl.
CPC ........ *A61B 17/2255* (2013.01); *A61B 17/225* (2013.01); *A61B 17/2251* (2013.01);
(Continued)

(58) Field of Classification Search
CPC ... A61B 17/2255; A61B 34/10; A61B 17/225; A61B 17/2251; A61B 2018/00648;
(Continued)

(56) References Cited

U.S. PATENT DOCUMENTS 4,972,826 A    11/1990   Koehler et al.
5,409,002 A    4/1995    Pell
(Continued)

FOREIGN PATENT DOCUMENTS

EP    0276385 A2    8/1988
EP    0377901 A1    7/1990
(Continued)

OTHER PUBLICATIONS

Waxler et al., "Effect of Pressure and Temperature on the Refractive Indices of Benzene, Carbon Tetrachloride, and Water" Journal of Research of the National Bureau of Standards-A. Physics and Chemistry vol. 67 A, No. 2, Mar.- Apr. 1963.
(Continued)

*Primary Examiner* — Hien N Nguyen
(74) *Attorney, Agent, or Firm* — Grossman, Tucker, Perreault & Pfleger, PLLC

(57) ABSTRACT

The present invention provides enhanced ESWL efficacy for therapeutic and operational outcomes. Device behavior and performance data is measured in-situ and analyzed for both intra-procedure and inter-procedure breadth of regard such that both therapy optimization and maintenance optimization engines are provided an accurate and current assessment of ESWL system and device state and performance. This feedback and control provides the ability to compensate in real time for the current patient therapy and offline for future patient therapy for machine/therapy idiosyncrasies and realize continuous calibration of system/devices to the performance required for maximum ESWL patient efficacy.

3 Claims, 15 Drawing Sheets

(51) Int. Cl.
*A61B 90/00* (2016.01)
*A61B 17/00* (2006.01)
*A61B 18/00* (2006.01)
*A61B 34/00* (2016.01)
*H03K 3/55* (2006.01)

(52) U.S. Cl.
CPC .......... *A61B 34/10* (2016.02); *A61B 17/2256* (2013.01); *A61B 2017/00022* (2013.01); *A61B 2017/00084* (2013.01); *A61B 2018/00648* (2013.01); *A61B 2018/00684* (2013.01); *A61B 2018/00988* (2013.01); *A61B 2034/256* (2016.02); *A61B 2090/376* (2016.02); *H03K 3/55* (2013.01)

(58) Field of Classification Search
CPC .... A61B 2017/00022; A61B 2034/256; A61B 2018/00684; A61B 2018/00988; A61B 2017/00084; A61B 2090/376; A61B 17/2256; H03K 3/55
See application file for complete search history.

(56) References Cited

U.S. PATENT DOCUMENTS

| | | | |
|---|---|---|---|
| 5,435,304 | A | 7/1995 | Oppelt et al. |
| 7,785,276 | B2 | 8/2010 | Bohris |
| 7,988,631 | B2 | 8/2011 | Bohris |
| 8,099,154 | B1 | 1/2012 | Wess et al. |
| 9,131,949 | B2 | 9/2015 | Coleman et al. |
| 9,820,762 | B2 | 11/2017 | Cadeddu et al. |
| 2004/0179332 | A1 | 9/2004 | Smith et al. |
| 2010/0113983 | A1 | 5/2010 | Heckerman |
| 2010/0137754 | A1 | 6/2010 | Zhou |
| 2010/0249671 | A1 | 9/2010 | Coleman et al. |
| 2012/0065553 | A1* | 3/2012 | Lebet ............... A61B 17/22012 601/2 |
| 2014/0074111 | A1 | 3/2014 | Hakala et al. |
| 2014/0081174 | A1 | 3/2014 | Owen et al. |

FOREIGN PATENT DOCUMENTS

| | | |
|---|---|---|
| EP | 0382392 A1 | 8/1990 |
| EP | 3047809 A3 | 7/2016 |

OTHER PUBLICATIONS

Haecker et al., "The role of focal size in extracorporeal shock wave lithotripsy," New Trends in Shock Wave Applications to Medicine and Biotechnology 2009.

Lindwall et al., "Acoustic-Elastic Scattering Predictions and Experimental Verifications Via Water Tank Experiments," Proceedings of the Seventh European Conference on Underwater Acoustics, ECUA 2004 Delft, The Netherlands Jul. 5-8, 2004.

Chaney et al., "Simple MOSFET-Based High-Voltage Nanosecond Pulse Circuit," IEEE Transactions on Plasma Science, vol. 32, No. 5, Oct. 2004.

Wendell Verner Swanson, "Electronic Pulse Generator for Thyratron Control, " Thesis submitted to Oregon State College, Jun. 1947.

EP Office Action from related matter EP 17832638 dated May 8, 2020.

* cited by examiner

EXTRACORPOREAL SHOCKWAVE LITHOTRIPSY (ESWL) SYSTEM AND METHOD USING IN-SITU SENSING OF SYSTEM AND DEVICE DATA AND THERAPEUTIC/SYSTEM/DEVICE LEVEL CONTROL

CROSS-REFERENCE TO RELATED APPLICATIONS

This application claims benefit of priority under 35 U.S.C. 119(e) to U.S. Provisional Application No. 62/443,164 entitled "Extracorporeal Shockwave Lithotripsy (ESWL) System and Method using In-Situ Sensing of System and Device Data and Therapeutic/System/Device level Control" and filed on Jan. 6, 2017, the entire contents of which are incorporated by reference.

BACKGROUND OF THE INVENTION

Field of the Invention

This invention relates to extracorporeal shockwave lithotripsy (ESWL) systems and methods, and more particularly for in-situ sensing and detection of system outputs and device operating parameters and implementation of therapeutic/system/device level control of the ESWL system to improve current and future patient therapies and to enhance efficacy of system maintenance.

Description of the Related Art

The objective of an ESWL (extracorporeal shockwave lithotripsy) system is to non-invasively apply acoustic energy to a patient kidney that induces fragmentation of a kidney stone(s) such that fragments of the stone(s) can be passed via the patient urinary tract.

The core of the ESWL system is the generation of therapeutic acoustic energy required for stone fragmentation. This can be viewed as a three step process: 1) acoustic energy is produced with an electrical power source, e.g., 20 kV high voltage, source that 2) excites an acoustic transducer with a short energy discharge controlled by an electronically controlled current switch, e.g., a thyratron; and 3) the acoustic energy from this discharge event is focused on the kidney stone inside the patient's body. Repeated application of this energy to the stone leads to fragmentation.

The remaining elements of the ESWL system address patient positioning, water flows and gas content control, airbag control and general signal and system timing and control, including the synchronization with patient respiration by way of electro-cardiogram (ECG) measurements. Water flow management is required because the acoustic signal path from the acoustic transducer to the stone must be aqueous throughout; gas carried in the water must be minimized and managed because excess gas in the water causes defocusing of the acoustic energy and other unwanted performance degradations. Airbags are present in the system so that, when the patient is being positioned so that ESWL energy is focused on the stone, it is helpful to use air to displace water along the path of the X-Ray imaging device used to observe the stone location with respect to the known ESWL focus.

An embodiment of an ESWL System 10 is depicted in FIG. 1 and its method of use in FIG. 2. Prior to the ESWL therapy, a patient 12 is placed on an integral ESWL Patient Table 14 (step 100). An operator 16 enables system functions and uses the ESWL system 10 by way of an Operator Control Panel 18 that connects directly to a System Controller 20 (step 102). After inflating a Central Air Bag 22 and a 30 Degree Air Bag 24 with an Air Pump and Control module 26 (step 104), a separate X-Ray imaging system (not shown) is used to locate ESWL focus with an X-ray image (step 106) and then align the focus of the ESWL Focusing Parabola 28 to the kidney stone (step 108) by moving the patient. The patient is moved using a Three Axis Patient Actuator 30 that is controlled with a Three Axis Motion Control module 32 until a kidney stone 33 is co-located with the ESWL focus in all three physical dimensions. Therapy proceeds upon operator command through the Operator Control Panel, after which action a Timing Controller 34 produces a recurrent sequence (~1 Hz) of signals to charge a Energy Storage Element 36 such as a capacitor using a High Voltage Power Source 38 (more generally an electrical power source), trigger a Thyratron Driver 40 to, in turn, activate a Thyratron Current Switch (Thyratron Tube) 42 (more generally an electronically controlled current switch) to discharge the stored energy into an Acoustic Transducer 44. This transducer is accordingly driven to produce an in-water displacement of water over the area of the transducer such that the resultant acoustic wave propagates via the Focusing Parabola 28, resulting in a high pressure, focused shock wave 46 being applied to the kidney stone 33.

The following paragraphs briefly describe exemplary embodiments of the ESWL system elements just delineated.

Patient Table 14 is suitably a planar surface large enough to safely support the patient's body while yet providing an opening for the patient to come in contact with a Coupling Cushion 48 that lies between the patient 12 and the ESWL Focusing Parabola 28. The table is a sturdy structure that currently must support patients up to 500 pounds. The table is supported by movable structures in each of the three physical dimensions; both electro-mechanical and hydraulic support structures are common in the marketplace. The table may have additional features such as a Trendelenberg support, which is useful for positioning patient legs during the therapy.

Three Axis Patient Actuator 30 that is part of the support structure for the Patient Table is made of three or more motors or hydraulic pistons (in the case of a hydraulic system), one or more for each axis of motion. The vertical axis, having a potentially high load, may be driven with multiple motors (e.g., a gantry arrangement) for mechanical stability and rigidity. Activating the actuator moves the table in one of the three possible directions.

The multiple axes of actuation are controlled through electronic means such as a motor controller and amplifier having motor or load feedback using a rotary or linear encoder that constitute Three Axis Motion Control 32. Such a servo-like arrangement allows for accurate and repeatable movements of the patient. Some systems allow for the motion control to be removed upon operator command such that the patient can be moved manually (a clutch mechanism for example, or a means of allowing motors to be back driven); this is sometimes helpful for quickly moving the patient into approximate position, after which time the precision of the motion controller can be used to make fine adjustments of the patient and stone.

A Circulation Water Pump and Control 50 circulates and continuously degasses water during therapy. Water is necessary throughout the acoustic path; this is inherent to ESWL technology. Degassing the water is necessary to assure optimum acoustic propagation and focusing. Approximately half the ambient concentration of dissolved gas (20 C, sea level conditions) is desired, so some degassing is helpful in general. However, the ESWL process also produces gas (air) in the water such that the gas content of the water will climb above nominal/ambient if degassing is not present. Finally, it is helpful to circulate water in the ESWL system to aid in cooling the acoustic transducer so that it does not overheat and so that, should the patient come into (indirect) contact with the transducer, no thermal damage to patient skin occurs; on the other hand, it is important to maintain warm enough water to support therapy (a familiar system uses 28 C as a target water temperature).

For these reasons an ESWL system uses two water pumps: one that circulates the water through the system and another that facilitates degassing. Also, the circulation pump system includes a water heating element and the degassing pump system includes a water chiller, e.g., radiator. Water pressure and motor velocity are monitored by a pressure sensor and tachometer and used to manage the height of the Coupling Cushion above the Focusing Parabola (representing an embodiment of a focusing element) and, in some cases, to allow for limited duty cycle motor operation to enhance motor lifetimes. The circulation pump circulates water from the base (lower portion) of the focusing parabola and the degassing pump circulates from the top of the parabola to the top of a Reservoir 52.

A Water De-Gasser 54 performs a degassing operation that involves capturing the gaseous water near the top of the Focusing Parabola (directly under the Coupling Cushion) and passing it into a chamber having a slight vacuum such that gas is pulled out of the water and allowed to escape by means of valves. The vacuum is maintained by controlling the differential water velocity into and out of the degassing chamber while allowing only half the volume of the chamber to be occupied by water. The water and air pressures needed to achieve degassing are managed by way of water and gas pressure gauges and valves in concert with the control of the degassing water pump.

Air Pump and Control 26 controls inflation of two air bags inside the Focusing Parabola, one of which is internal to the Acoustic Transducer (Central Air Bag 22) and the other of which is adjacent to the transducer (30 Degree Air Bag 24). The purpose of these air bags is to push water out of the X-Ray optical path during X-Ray imaging to minimize the radiation dose and also to improve the X-Ray image quality. There are two bags to accommodate two different X-Ray viewing angles. The air bag inside the Acoustic Transducer is co-axial with the acoustic focusing; the air bag adjacent to the transducer is oriented along a 30 degree path that allows for off-acoustic-axis X-Ray imaging of the focus. The operator adjusts the size of either bag by adjusting the air pump speed and using a valve to select which bag is pressurized; a common motor and controller thus provides air pressure for both bags. Control valves are used to select the bag to pressurize and bag pressure is determined by a predetermined runtime for the pump motor.

High Voltage Power Source 38 is an electrical power source, e.g., 20 kV high voltage, power supply having a programmable voltage set point. The voltage is set by a 4-20 mA current loop. It is also monitored inside the high voltage supply using a voltage divider; this is reported with a 4-20 mA current loop. By comparing both the commanded and reported voltage, the set point is held constant by feedback and control circuits. The high voltage power supply can be inhibited by a logic level control input (high voltage inhibit) and outputs a logic level control signals indicating that it is fully charged to its set point.

Energy Storage Element 36 e.g., a high voltage capacitor, provides the means of storing energy for generating period shock waves. For parabolic focusing geometry based on a cylindrical acoustic transducer, a capacitor of approximately 1 uF is paired with the (nominal) 20 kV power supply. Prior to discharging the capacitor through the Acoustic Transducer, the capacitor is charged by the high voltage power source. The capacitor is designed into the system with multiple bleed resistors of approximately 100 Mohm connected across the leads of the capacitor to enable a passive means of discharging the capacitor; this facilitates patient and operator safety.

A thyratron is an embodiment of an electronically controlled current switch and is electron tube device capable of switching very high currents (in this case, approximately 10000 Å), and at high voltages. For this ESWL system, the thyratron is connected across the series combination of high voltage capacitor and Acoustic Transducer. When the thyratron plasma has been established and a trigger voltage is provided to the thyratron gate, the plasma becomes conductive, closing the "switch" (Thyratron Current Switch 42) by way of connecting cathode and anode through the conductive plasma, which typically produces an emission of photons, or light. This then places the high voltage, up to 20 kV, across the acoustic transducer for the duration of the trigger voltage, generating an approximately 6 microsecond wide, 10000 ampere current pulse through the transducer.

Acoustic Transducer 44, as shown in more detail in FIG. 3, is used to originate the acoustic wave inside the Focusing Parabola 28. The transducer includes a cylindrical air core transformer ("Coil") 60 with approximately 30 turns of wire on its primary wound around a plastic bobbin and a single turn of cylindrical copper sheeting approximately 0.004" thick on its secondary enveloping the primary. By exciting the primary with the current pulse via the thyratron, a very high current is produced at the secondary. These two currents produce high intensity opposing magnetic fields such that the secondary is pushed away from the primary for the duration of the current pulse, approximately 6 uS. The resultant displacement, taking place inside the water volume and within the focusing element, embodied here as a Focusing Parabola, originates an acoustic shock wave 62. Focusing Parabola 28 focuses the acoustic shock wave 62 to focused shock wave 46 at a shock wave focus 66 (coincident with the patient's kidney stone).

Focusing Parabola 28 surrounding the Acoustic Transducer serves to focus the acoustic wave toward the shock wave focus 66 that is more than 10 cm away from the upper edge of the parabolic focusing element. The parabola is metallic, e.g., brass, and has openings at its base for water circulation and principally, for the apparatus that supports the transducer.

The Patient Table positions the patient for focusing the ESWL system on the kidney stone of concern. Between the patient and the ESWL focusing parabola is a cushioning polymer (Patient Volume with Coupling Cushion 48) that, accordion-like, allows for some flexibility in the distance between the stone and the perimeter of the patient's body. The polymer is chosen to have a density close to that of water for minimizing acoustic reflections. The patient rests in a water bath held by a polymer sheet in a depression surrounding the area where the parabola approaches the patient volume so that, at all times, acoustic energy is only traversing acoustically transparent material having a density close to that of water. Where water cannot be contained easily, e.g., at the interface between polymer sheet and coupling cushion, coupling grease is used to match acoustic impedance.

The formation of focused shock wave 46 begins with the electromagnetic excitation of the acoustic transducer 44 with a short, high-energy pulse (i.e., discharging a high voltage capacitor in the Acoustic Transducer 44). The high energy and short time scale produce a displacement of water that propagates at ultrasonic speed. The cylindrical transducer 60 initially produces a cylindrical displacement ideally having a uniform distribution along the length of the cylinder and around its circumference. By locating this transducer in a parabolic reflector 28, the shock wave 62 is focused at a predetermined distance from the parabola to form the focused shock wave 46—this is a consequence of the geometry of a parabola. As the shock wave comes to a focus, the pressure rises, leading to an increase in velocity—this is characteristic of shock waves. The shock wave interacts with the kidney stone by, in turns, exposing the stone to compression and tension, whilst also producing cavitation locations that serve to erode the stone.

The shock wave 46 comes to a focus that is on the order of one millimeter transverse to the acoustic propagation and on the order of one centimeter in the direction of propagation. The width and depth of the focus can be varied by adjusting the high voltage charge capacitor value, if this is provisioned, e.g., a switchable bank of capacitors. The operator can also vary the intensity of the shock wave 46 by adjusting the amplitude of the high voltage power source used to charge the high voltage capacitor; varying the amplitude of the high voltage power source also affects the size of the focus zone, primarily in the transverse direction and inversely with respect to the high voltage amplitude. Finally, the operator may adjust the frequency of shock wave events, e.g., 0.5 to 2.0 shocks per second, and the number of shock waves generated.

As with any physical device, the use of the ESWL system over time produces variations in performance due to varying factors such as environment, wear and tear (component degradation), and the inherent variation of system components and their interactions in producing therapeutic outcomes. System performance variation can also occur due to the inevitable time variation of all physical systems; one day's behavior may vary from the next due to factors that are unknown or yet-to-be-quantified, e.g., system water chemistry or age, acoustic transducer windings temperature, instantaneous and local gas content of water in acoustic path, etc. These are intra-system performance variations. Variation that is a reflection of component or system imperfection may also occur, when an ensemble of systems are considered as a population (inter-system variation). These variations in system performance will affect therapeutic and operational efficacy.

Systems today are able to achieve 75-85% efficacy routinely with relatively infrequent system failure rates, provided significant expense in bi-annual maintenance functions and rapid service response is sustained and adequate care is exercised in assessing patients for ESWL procedures.

ESWL system manufacturers use the periodic system maintenance function (e.g., bi-annual) to regulate the performance of systems by confirming that intended set points (e.g. the high-voltage set point, air and water systems set points for limit switches and valves, limit switch set points for electromechanical components, capacitor capacitance, thyratron heater voltage set point, high voltage 4-20 mA current loop control current levels, earth ground leakage current levels, patient leakage current, x-ray focus location, therapy shockwave focus and dummy stone response,) are being reached. Adjustments are recommended as part of maintenance to retain compliant performance at the service times.

SUMMARY OF THE INVENTION

The following is a summary of the invention in order to provide a basic understanding of some aspects of the invention. This summary is not intended to identify key or critical elements of the invention or to delineate the scope of the invention. Its sole purpose is to present some concepts of the invention in a simplified form as a prelude to the more detailed description and the defining claims that are presented later.

The present invention provides enhanced ESWL efficacy for therapeutic and operational outcomes. This is accomplished by continuously measuring and analyzing ESWL system and device behavior/performance data for both intra-procedure and inter-procedure breadth of regard such that both therapy optimization and maintenance optimization (compute) engines are provided an accurate and current assessment of ESWL system and device state and performance. This feedback and control provides the ability to compensate in real time for machine/therapy idiosyncrasies and realize continuous calibration of system/devices to the performance required for maximum ESWL patient efficacy.

In an embodiment, sensors are embedded in-situ in the ESWL system. The sensors are configured to sense data including operating parameters and outputs of a plurality of the ESWL devices. Data is captured from the sensors during operation of the ESWL system to produce the focused acoustic shockwave, either during calibration or patient therapy. The data is stored locally in the ESWL system and communicated to a remote location where data from multiple ESWL systems is aggregated. The data is processed locally or remotely to update therapy or maintenance models to provide feedback to the local ESWL system to implement one or more of therapeutic, system and device level control of the ESWL to enhance efficacy of a given patient therapy or future patient therapies or to enhance efficacy of ESWL system maintenance.

These and other features and advantages of the invention will be apparent to those skilled in the art from the following detailed description of preferred embodiments, taken together with the accompanying drawings, in which:

DETAILED DESCRIPTION OF THE INVENTION

Figure 1:
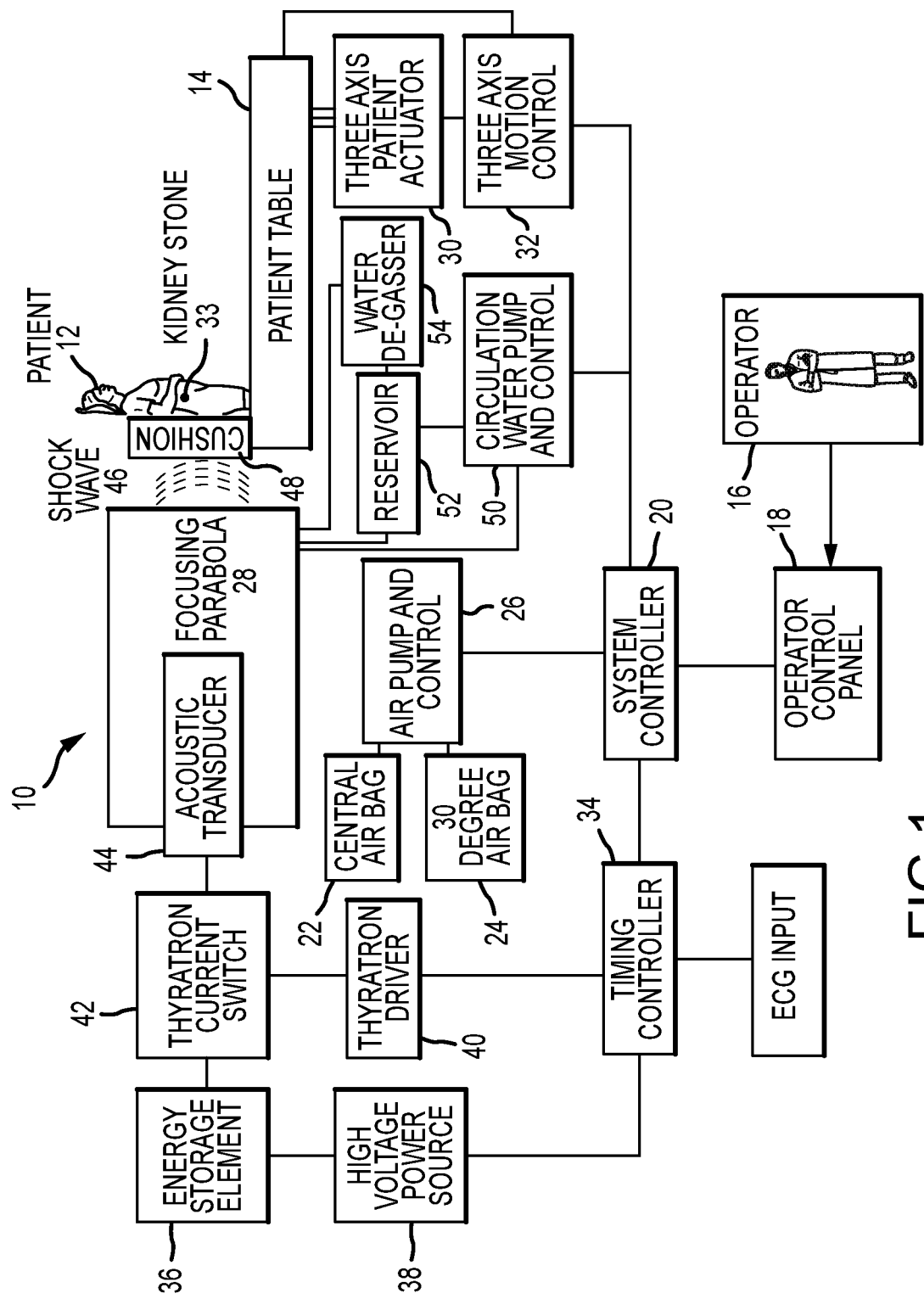
FIG. 1, as described above, is a block diagram of a known ESWL system.

Practitioners and providers of systems to medical care providers may collect the service data and use it to estimate time of failure; the primary failure-estimation data, however, are actual failure events, and these are used to inform statistical models of mean time to failure (MTTF) and related measures (e.g., Weibull distribution calculations, using a tool such as Weibull++ from Reliasoft Corporation).

Variations in ESWL system performance due to environment, component degradation, variation in system components (e.g., devices) and interactions of these variations will affect therapeutic and operational efficacy. Since efficacy is the essence of patient care, it is important to understand, quantify and compensate for these variations in order to obtain maximum efficacy.

The fact that efficacy can yet be less than 90% and unexpected field failures of systems do occur with some frequency suggests that system variability can be reduced and/or compensated if appropriate measurements and derivative controls/calculations/algorithms are used to affect the use and maintenance of systems and their components.

In a complicated system, using system or major component failure data to predict future failures will be only as successful as the underlying data are statistically significant, robust and exhaustive. The ESWL system cost discourages any single provider from having enough systems to support robust statistical assessments based only on the relatively infrequent and data-sparse maintenance cycles and/or failure events. Even ESWL syndicators having 10-100 systems may not have adequate data to support a model based on failure statistics, since significance of measurement will also imply a very low performance level that may preclude staying in business. For those that collect procedure-based data, those patient-centric data and records are the primary elements, at present, that offer significant statistics, especially if multi-year or multi-decadal data are collected and used.

At present, data concerning the system state and performance within procedures and on a shot to shot basis are not collected in-situ or used within the system to produce system efficacy outcomes. These (internal) system state data do produce changes in outcomes; however, since system state data are not available, the variations of the system are carried (statistically) by other system variables such as location, system serial number, physician and/or technician identity, etc.

For instance, when using an ensemble of systems that are operated at a particular high voltage level (e.g., level 1, 2, 3, . . . 7, corresponding to 12, . . . 20 kV), the actual high voltage used is not actually measured when the operator sets the level. There is regulation circuitry to maintain a nominal high voltage set point, but there is not a mechanism in place to address possible drift within a system over the course of a procedure, nor to capture the shot to shot variations in actual applied high voltage, such as will occur when the frequency of therapy is changed from 0.5 Hz to 2 Hz, for instance. The same is true of the current flow through the thyratron; existing systems do not measure this during maintenance or therapy, though this current is a primary determinant of the energy delivered and the focus produced at the stone location. It is assumed that the requested levels of voltage and current and their respective temporal responses are constant over time and do not vary with time once set. It is also assumed that a level setting on one machine will produce the same therapeutic physical phenomena as that same level setting on another machine.

In short, while it is known that the drift in operational levels for physical parameters affecting therapy (e.g., voltage, current, water pressure, dissolved gas, shockwave energy, etc.) is non-ideal, there are no mechanisms to capture and compensate for such non-ideal behavior outside of a periodic maintenance that recurs on a span of hundreds of procedures and as much as a million shockwave events. Further, as these physical parameters are some of those having a bearing on system and subsystem lifetime and failure, there are also no in-process ongoing measurements in systems to support predictive maintenance and failure prevention based on measured system or component health, aside from infrequent maintenance events.

The data that is captured during an ESWL procedure from the ESWL system can be used both to enrich existing, proven statistical models of therapy efficacy as a function of system level inputs or system health/status and to improve system parametric/physical consistency during a procedure. The statistical models are updated by virtue of the inclusion of new information for a new patient and a system that is one therapy older—all the data are in some sense new and informative. Enriched statistical models will inform more accurately the probability of equipment failure in the future and the probably that a given patient will have a successful therapeutic outcome.

Figure 12:
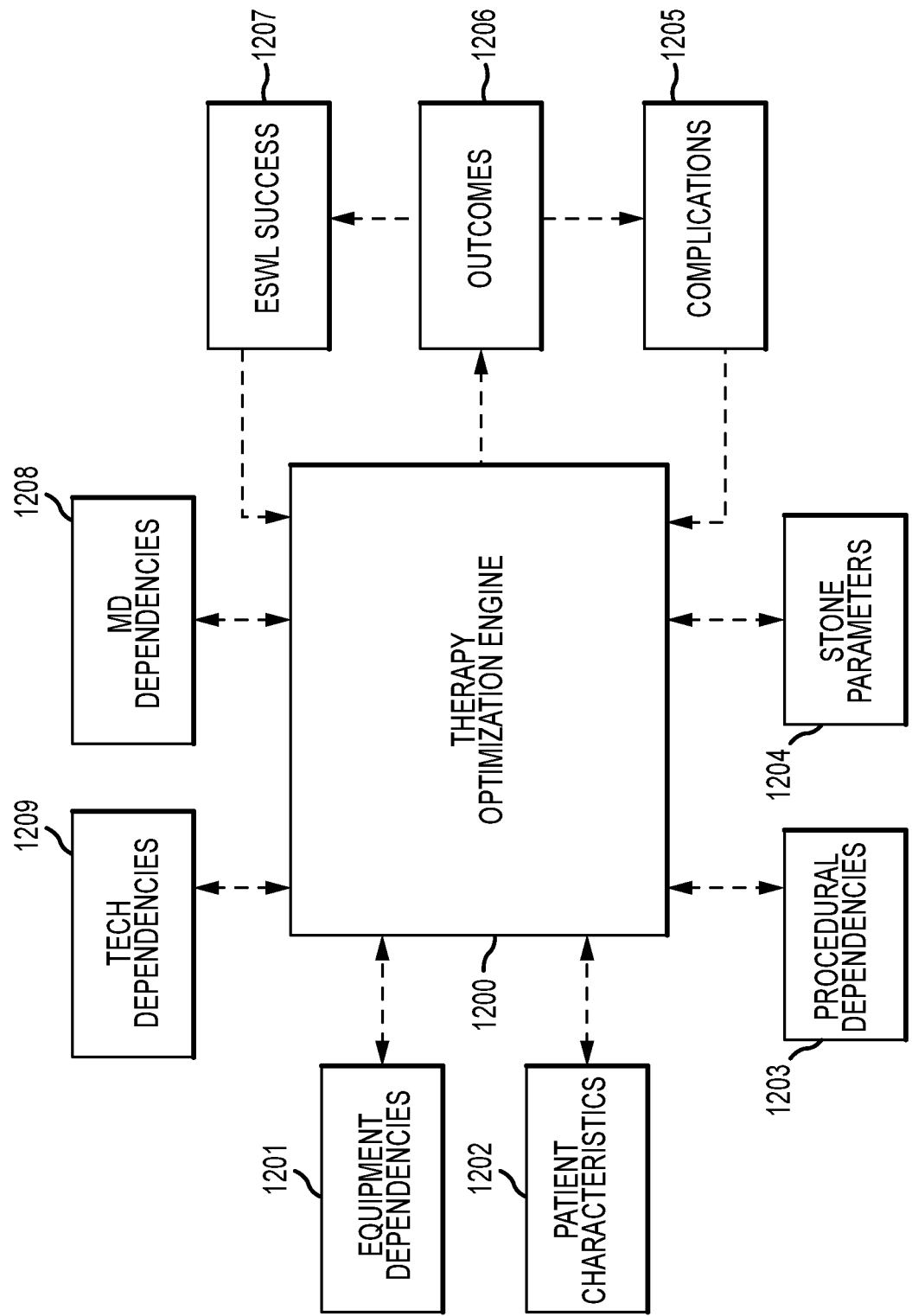
FIG. 12 is a simplified diagram of the inputs, outputs and, for some elements, feedback, for an ESWL therapy optimization engine used to optimally attune therapy settings to the patient, physician, technician and equipment condition.

For example, FIG. 12 shows an example flow of inputs and outputs for a statistical model that is constituted as a Therapy Optimization Engine 1200. Such a statistical model is built, for example, by gathering outcome data 1206 as a function of all factors in a therapy that affect outcomes (either ESWL Success 1207 or Complications 1205), e.g., Patient Characteristics 1202, Procedural Dependencies 1203, Equipment Dependencies 1201, Tech(nician) Dependencies 1209, MD (medical doctor) Dependencies 1208, and Stone Parameters 1204. Given a statistically significant body of data having variations in its various inputs and at the primary output (Outcomes), the outputs and inputs can be related by vector or tensor operators as $$D = f(T, I)$$

Where D is the decision vector (Outcomes, of which there are two, for this example), T is the Therapy Optimization Engine operator, thereby constituting a form of therapy model, and I is the vector of input data (it is implicit in this discussion that T can be determined using a statistically significant set of data having varying Dependencies or inputs, and Outcomes or outputs). Using one of many available techniques, e.g., regression, pseudo-inverse, or machine learning, the relationship can be inverted so that the Inputs are solved for as $$I = f(T, D)$$

Using such a framework, one may compute, using the body of data collected, combinations of inputs that produce a given output, e.g., ESWL Success, or that minimize the likelihood of an output, e.g., Complications. Such a computation, or processing of inputs and outputs using a therapy model constitutes an optimization engine that can be used recurrently and can be improved over time as data and learning accumulate. Alternately, the framework and associated data may be used to compute probable Outcome states when some inputs are varied while other inputs are held constant. For instance, the optimum set of equipment dependencies might be computed given fixed Patient, MD or Tech Dependencies (inputs). Alternately, a Complication probability might be estimated for a given Patient and Stone condition as a function of Tech, MD or Equipment, so as to produce a recommended minimum-Complication condition of therapy for the patient. The possibility of determining boundaries for inputs based on other inputs and outputs is the basis for having arrows in both directions for input data (Dependencies and Parameters) shown in FIG. 12. Consequently, therapeutic control, that is to say, the control of the nature or level of therapy administered to a patient, can be achieved by using a statistically significant body of data regarding system inputs, system outputs and therapy related inputs or outputs to solve for therapy constraints or settings at any given input or output such that control is maintained over optimizing efficacy.

Likewise, knowing the actual system/component state and how this relates to outcomes for a particular patient during a procedure opens an opportunity for adjusting the settings to improve the outcome. Such an adjustment would be needed, for instance, when a component set point is held as set but a related and unobserved component varies, leading to outcomes away from the set point. For example, if the high voltage components provide exactly the requested output but the energy storage capacitor begins to age and exhibit altered reactance or equivalent series resistance, the discharge pulse may vary from its norm, thereby producing a therapy different from the desired one. In this case, the data captured during the procedure enable the use of the high voltage supply setting to compensate for the capacitor aging.

In-Situ Sensing & Communication of Set-Points and Device Data

Figure 4:
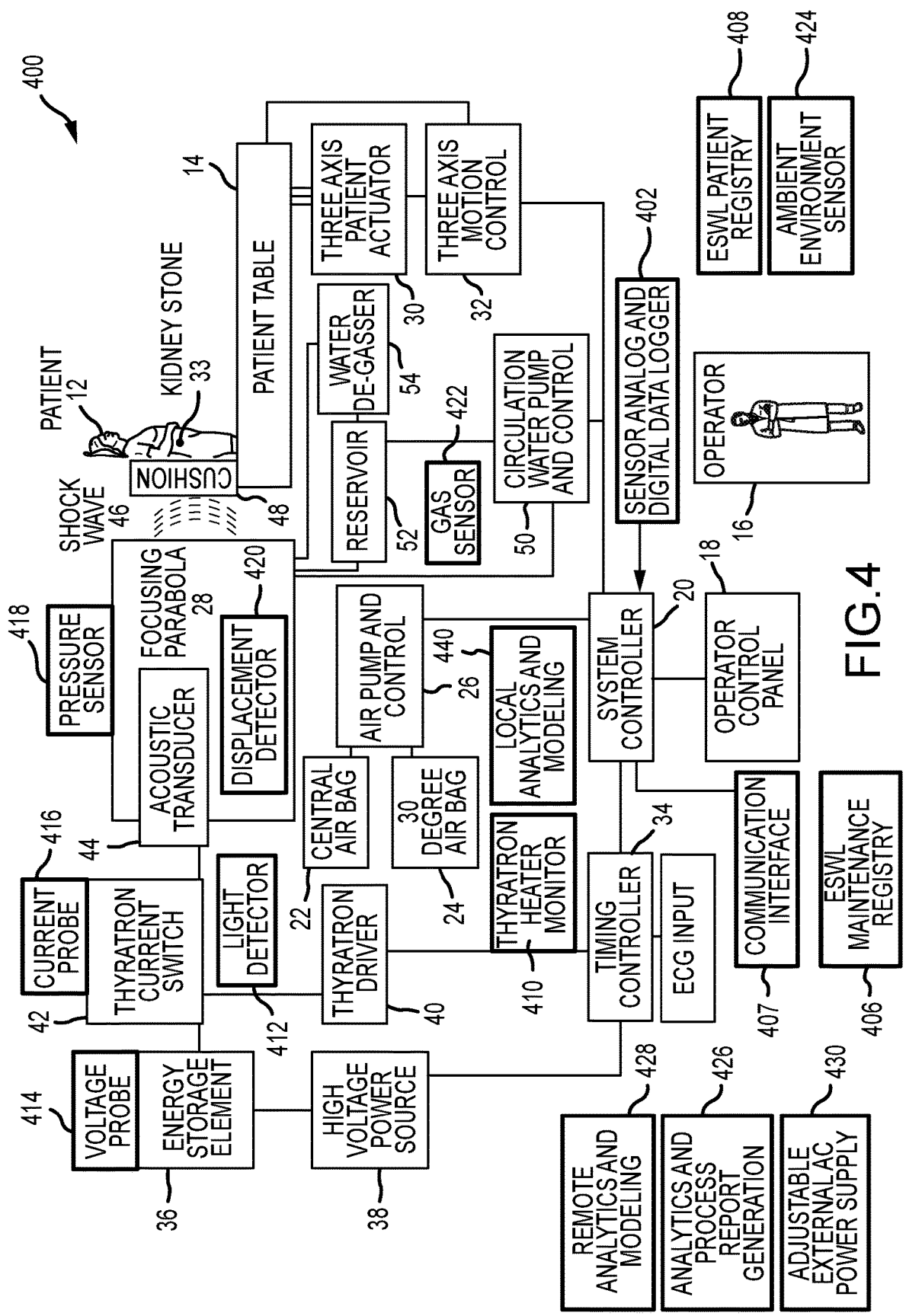
FIG. 4 is a block diagram of an embodiment of an ESWL system provided with a system of sensors for sensing in-situ device and system data.

In accordance with the invention, an in-situ sensing network 400 of sensors and detectors is configured to sense or detect operating conditions of various components (devices) of the ESWL system and to record, report and possibly cause the ESWL system to act on the operating conditions to improve efficacy of the patient therapy as illustrated in FIG. 4. In this embodiment, the underlying ESWL system is that shown and described in FIG. 1 using the same reference numbers for clarity and brevity. Other configurations of an ESWL system are known to produce a focused acoustic shockwave. Appropriate sensors may be embedded in the system to provide the requisite data for therapeutic/system/device level control.

Analog and digital sensor and detector data is collected at a system controller (or a companion controller) and is used for real-time and offline data processing tasks aimed at efficacy management and improvement.

Sensor data is captured and time stamped with a Sensor Analog and Digital Data Logger 402 before being forwarded to the System Controller 20 that aggregates the data locally and formats it for appending to a database, e.g., a relational database (RDB) such as SQL or a non-SQL variant such as Mongo. Data during procedures are aggregated on a per-shot basis, e.g., in a JSON data file. Some data are singleton values and some are arrays of values, usually corresponding to a time series, e.g., "scope trace" of a time varying waveform. Once formatted, data are stored locally in non-volatile memory at minimum, and can be forwarded and logged to an ESWL Maintenance Registry 406 and/or ESWL Patient Registry 408 at convenient times during a procedure or at the conclusion of the procedure, such data transfer being accomplished using a Communication Interface 407, in which case a network memory buffer device/structure may be used to prevent adverse impact of occasional local network outage due to high EMI (electromagnetic interference) conditions.

For embodiments that have a thyratron as an electronically controlled current switch, the thyratron heater operation is monitored with a Heater Monitor 410 that senses the voltage and current delivered to the heater (the "reservoir", as it's described in datasheets), e.g., by measuring the voltage across the input to the heater (heater voltage) and also the heater current by measuring drop across a small current sensing resistor placed in the current path of the heater by way of a differential amplifier, or indirectly by measuring the alternating current input line voltage to the system (the same voltage that is used to power the heater subsequent to an electrical transformer) and comparing it to nominal/expected values, e.g., for voltage one expects 230 VAC for typical North American installations, such that an Adjustable External AC Power Supply 430 can be adjusted, e.g., manually or via electronic control, or the transformer supplying the Thyratron Heater can be adjusted, manually or via electronic control (by way of using a programmable transformer component).

The Thyratron Heater Monitor 410 captures the current through and the voltage across the heater element of the Thyratron Current Switch 42. For optimum lifetime and performance, the thyratron must operate within a narrow voltage and current range, e.g., within five percent variation of voltage on 6 volts and 22 amperes. As the thyratron directly affects the energy transfer to the stone, its effectiveness is important to measure. One way to assess effectiveness is in the quality of the charge plasma produced by the ionized gas (e.g., hydrogen or deuterium) inside the thyratron tube when it is energized; this ionized gas cloud inside the tube is enabled by the heating of a gas generating element in the tube, and there is an optimum amount of gas for effective tube operation. The known Paschen curve for hydrogen relates the plasma breakdown voltage to the thyratron electrode space and gas pressure in the tube; given a tube geometry, the breakdown behavior will track with gas pressure in a known way and an exponential rise time will be produced for the thyratron current.

If the heater is not operating optimally, the thyratron will either provide too little current or too much current over time, leading to premature failure, inconsistent thyratron response rise time (gas density in the thyratron grid/anode gap is proportional to rise time) or unintended discharges (typically a secondary discharge immediately subsequent to the primary and intended discharge). Digitizing and storing its heater voltage and current enables this aspect of thyratron performance to be measured and managed, either a proactive or reactive correction—knowing the current waveform of the last pulse and its thyratron heater current state enables either a correction to produce a new output current behavior (proactive) or a the knowledge of existing behavior enables a better interpretation of outputs (reactive). Correction can be achieved by directly altering the thyratron heater voltage using active electronic elements, or for instance, by changing the system input AC line voltage such as might be achieved using a programmable uninterruptable power supply that can be sent such control commands by the communication interface of the invention. If it is known that the thyratron heater element is accepting energy properly, then only the input voltage is needed to assess its performance; however, a more complete measurement assumes nothing about its health and captures both the voltage and current delivered to the thyratron heater element.

The system level model incorporates this data so as to adjust the expected energy level produced by way of the thyratron current, for example. The device level model makes use of this data (in combination with system and thyratron thermal state) by, for instance, adjusting the expected lifetime of the thyratron to reflect an optimum or suboptimum current setting. An excessively low current reading would trigger an operator warning and may preclude therapy, since the thyratron will cease to function properly if the heater-dependent plasma inside the thyratron tube is not fully present; alternatively if the desired therapy benefits from an increased rise time on the current (more aggressive resultant pressure wave), the thyratron gas pressure may be operated near the upper end of its allowed levels so as to adjust the peak therapy pressure at the system focus. If the required adjustment is within range of adjustment and does not suggest a larger problem, the auto-calibration (e.g., FIG. 9) features of the invention will allow for either a manual or automated response and adjustment of the current.

For embodiments that have a thyratron as an electronically controlled current switch, a Light Detector 412 [e.g., Thorlabs PSD with laser or LED illuminator such as the PDQ80A] placed within line of sight of the thyratron tube measures the light output (photons) from the plasma when the tube is triggered with the Thyratron Driver. If a photon detector capable of accepting and measuring high energy photons is used, the X-Ray emission from the thyratron may be observed. The amount of X-Ray emission can be used to estimate commutation losses in the thyratron, which are a result of electrons failing to collide with gas molecules in the tube (X-Rays are generated when these energized electrons strike the metallic electrodes). It is normal to observe such light during shock wave generation. By measuring the amount and presence/absence of light during the trigger process, the health and well-being of the tube can be assessed. This assessment may be used, for instance, in conjunction with other measurements, e.g., thyratron heater voltage and current, to indicate a need for adjusting controlling factors of the thyratron light output, e.g., the amount of gas available in the tube to form a charge plasmas, such gas being proportional to the applied thyratron heater voltage (and resultant current). Measuring the behavior of light over time (i.e., the regularity of the light occurring, its intensity, its variation, its spectral content) can be used to assess the health and well-being of the thyratron as compared to its own prior data or the historical data for other thyratron tubes for the Light Detector measurement. Measuring the behavior of such light over time may also be used to detect a so-called double pulse of a thyratron, wherein two thyratron events are triggered when only one trigger signal was given to the thyratron. In this case, observing a rapid succession, e.g., 50 milliseconds separation in time as compared to a nominal 500-1500 milliseconds, may indicate a double pulse event. It is known that double pulse events can correspond to suboptimal gas levels in the thyratron, in which case the double pulse event may be prevented by controlling the thyratron heater voltage and current by means of either the Adjustable External AC Power Supply or a thyratron heater voltage transformer adjustment, e.g., either electronic, for electronically controlled transformers or manual, for manually adjustable transformers such as those with multiple secondary windings to choose from.

Excessive X-Ray emission may be used to trigger an operator assessment of tube life/health. Inconsistent light emission or statistically abnormal (i.e., as compared to laboratory calibration statistical data collected when the tube was newly installed in the system) can be used to indicate excessive heating in the thyratron or may be an indicator of failing trigger or high voltage supply electronics (use of companion voltage and current data would disambiguate in such a case). If feedback is provided to high voltage subsystem electronics, the absence of light may enable active adjustment for energy, timing, or related operational parameters of the Thyratron Driver and tube. The system level model uses this information to adjust its assumptions about the consistency of ESWL energy per shot, which may for instance produce operator guidance to compensate the therapy settings such as the number of shots required for fragmentation. The device level model is able to use this information by updating its reliability statistical data such that the lifetime estimate for the thyratron tube is updated for actual in-procedure behavior, e.g., by communicating performance data to a statistical assessment engine via network using a tool such as the Synthesis API (Reliasoft Corporation), such that updated probabilities and/or likelihoods can be inferred from data sent to this assessment engine.

In embodiments that require high voltage for the electrical power source, a High Voltage Probe 414 is used to measure the discharge waveform from the energy storage capacitor for a generated shockwave. This probe, e.g., Northstar High Voltage PVM-12, is a high voltage analog of a typical oscilloscope probe, designed to measure non-invasively and, in a preferred embodiment, optionally having built in self-protection for its circuits and the high voltage power supply used for capacitor charging. Measuring the waveform provides both the actual set point achieved prior to triggering, and also captures the shape of the discharge, which indicates the state and behavior of the load, which is dominated by the cylindrical transducer used to produce the shock wave. If an incorrect set point is observed at the output, the auto-calibration capability of the invention (e.g., FIG. 9) enables the manual or automated adjustment of levels.

For system and therapy modeling, the statistics of the high voltage waveform over the entire therapy indicate the consistency of the ESWL therapy energy (e.g., proportional to voltage squared, or when possible, the product of voltage prior to discharge and the peak current measured for the thyratron during discharge). The shape of the discharge waveform indicates the condition of the load (thyratron and transducer) and is used, for example, for monitoring the health of the power supply, thyratron and transducer; device modeling uses this information for informing maintenance and replacement cycles.

A Current Probe, e.g., Pearson Electronics Model 101, 416 is mounted on the output electrode of the thyratron such that the current passing from the thyratron into the Acoustic Transducer passes through the probe, which is a current transformer. Capturing the current waveform associated with shock wave generation indicates the actual behavior of the load, the Transducer. Combining this with the voltage probe data yields the time varying energy delivered by the thyratron and energy storage capacitor to the transducer (a transformer with cylindrical geometry).

The amplitude and width (shape) of the current probe waveform indicates the instantaneous energy produced and also the size of the focus. A wider pulse corresponds to a larger focus depth. For instance, in one solution, a 6 microsecond current pulse width, measured as the time between the onset of the current pulse and the time of the zero-crossing subsequent to achieving peak current, e.g., akin to the first half cycle of a zero-initial-value damped sinusoid, produces a focus spot size of 6 mm by 28 mm in diameter and focus-axis depth, such diameter and depth being measured as the half power points of the approximately Gaussian central lobe of the two dimensional acoustic shockwave energy distribution at one focal length from the focus element. For the same system, a 12 microsecond current pulse width produces a 9 mm by 50 mm focus. Thus knowing the waveform and using it to compute the pulse width produces a measurement of the energy distribution at the focus, all other things being the same.

By modeling the physics of the resonant circuit formed by the (capacitive) voltage storage element in parallel with the (inductive) acoustic transducer and measuring or calibrating the relationship between current pulse width and focus characteristics while also monitoring the other measurable of the system (e.g., the high voltage amplitude, device temperatures, etc.) the focus can be predicted for each shockwave event using, for example, a simple regression relationship between focus size, current pulse width, and other system variables.

The therapy model uses stone size to set parameters that drive the focus, for example, so waveform statistics enable model compensation for stone size. For instance, some practitioners will adjust the size of the focus between one of two settings available (using the aforementioned two-state system as an example) based on stone size and density, such stone parameters estimated from X-Ray data and/or other sources of information available to the physician from the patient or medical instrumentation.

Likewise, the total therapy energy levels relate to the number of required shots, in part, so the therapy model incorporation of current waveform data helps to optimize shot count and help minimize patient tissue bruising. For example, one therapy strategy is to use the total energy delivered to the stone as a measure of progress, in which case summing the known (measured) energy per shot over all shots can produce a different result than assuming the requested energy per shot is identically equal between and across all shots delivered during the therapy (it is known that energies vary over time and per shot event). Using such an actual total therapy energy for therapy decision making will improve the accuracy of therapy predictions that use the total energy as a key performance indicator.

At the device model level, current waveforms indicate the electrical character of the coil and are connected with its health, its reactance and its resistance. The same is true for the capacitor that stores charge and supplies a large current to the coil once the Thyratron is triggered and connects the capacitor electrically to the coil (an inductor). For instance, using some time during the system initialization or during known idle periods for the system, the high voltage can be applied to the capacitor so as to charge it, and then the high voltage probe can be used to measure the discharge time of the capacitor as it discharges through known safety resistors that are part of its circuit. This discharge time is a direct measure of the capacitance, holding other elements constant. This capacitor value, combined with the measured current waveform, can be used to estimate the inductance of the coil when the thyratron is turned on, by using equations from circuit nodal analysis.

Using Q=C*V where Q is the total charge given by the integral of the current waveform, C is the capacitance measured during system initialization, an estimate of the voltage waveform can be obtained and compared with the known/measured voltage to assess system consistency (laboratory characterization prior to placement of the system in therapeutic use serving as a reference point against which such assessments of goodness can be made), before proceeding with in situ and a priori measured circuit parameters to calculate remaining/implied circuit parameters, including the coil inductance. Significant deviations of such derived measurements can be used to assess health and well being of the system and/or its components. Thus, knowing the voltage, current, and other data such as the pressure allow for prediction of wear and tear at the coil and elsewhere, since the components are coupled and the physical behavior is well known and, in any case, can be characterized and modeled robustly using laboratory procedures.

One or more Pressure Sensors, e.g., PCB Piezotronic 119M31B with 402M136 charge converter and 482A21 amplifier, 418 are mounted on the outside wall of the Focusing Parabola, a parabola being representative of a conic section for focusing as this is not the only shape that can be used for focusing, such that it is sensitive to the pressure gradient produced by the shockwave initiated by the Acoustic Transducer. Measurement of pressure waveforms indicates the displacement achieved in the transducer with the thyratron current supplied with the high voltage capacitor. By carefully measuring the waveform as a function of known currents, voltages and focus-zone pressure measurements, a model, for example a linear relationship between pressure at focus (Pf) and the pressure at the bowl (Pb) expressed as $$Pf = b(V,I) + m(V,I) * Pb$$

Where b(V,I) and m(V,I) are regression coefficients for bias and slope of the linear relationship expressed as functions of the high voltage nominal value, V, and the peak discharge current through the thyratron, I, and such a function or mapping can be applied to relate the measured bowl pressure waveform to the achieved shock wave pressure at the focus. In so doing, an indirect measure of the shockwave can be made at each shockwave event. Further, given such a model that relates V, I and Pb to Pf, and given at least a measurement of one of V, I or Pb, an estimate may yet be obtained for Pf if the variables not measured, e.g., V and I if Pb were the measured quantity, using assumed values based on known operator intentions or settings. Using partial measurement data may not produce as accurate a result as using complete measurement data for this model, but it will nonetheless produce a more accurate estimate of Pf than for the case where all inputs to the model must be assumed.

At the therapy model level, this means the actual therapeutic dose of energy can be estimated based on one or more pressure measurements (more measurements allow for higher fidelity capture of the distribution of energy around the circumference of the focusing parabola) and accompanying voltage and current data. Knowing actual doses provides opportunity for improving long-term efficacy/settings in the model and also for improving a given procedure by way of operator interruption or signaling to consider an adjustment. The system models benefit from the pressure measurements when the pressure produced is compared with the energy applied to the transducer; if for instance, there is much more energy applied than is suggested by the pressure data, then the operator is alerted to the need to verify performance before continuing. If the aberration between expected and actual pressure is small, the operator alert may only be that of a need for maintenance, in which case the device level model is used to assess the maintenance schedule and approach based on the severity of the measurement discrepancy.

A Displacement Detector, comprised of a light emitter and position sensing detector, e.g., Thorlabs PDQ80A, in the case of direct position sensing, or a Sony IMX174 based CMOS camera in the case of structured light detection, 420 is designed to measure the movement of a transformer secondary cylindrical conductor that is the outermost layer in the acoustic transducer. This movement is the displacement that provides a pressure gradient that is the shockwave. Measuring its amplitude and distribution allows the estimation of the pre-focus shockwave character at each shockwave event. The amplitude of the displacement, when combined with estimates of the current and voltage used to drive the acoustic transducer produces an estimate of the transducer efficiency, e.g., in micrometers per Watt ($\mu$m/W), or equivalent measure of acoustic displacement per unit energy, where the displacement is indicated directly from the Displacement Detector and the energy is estimated using the voltage and current used to drive the transducer. This data and related model based estimates of performance and state allows real time control and/or monitoring of efficacy, or how effectively the transducer converts electrical energy into acoustic energy is, ultimately, applied to the kidney stone. In one implementation, the detector uses structured light illuminating the transducer cylinder and a nearby detector (e.g., small CMOS camera) to record movements in the imaged light structure; integration of this structure while illuminating with a continuous wave source (e.g., LED, laser) provides a measure of displacement using the 3D geometry of the arrangement and pixel measurements of intensity movement (i.e., fattening of lines during integration will indicate their movement). In another implementation, a laser point source illuminates the outermost Kapton-over-Copper layer of the acoustic transducer, e.g., a cylinder, and the reflected light is captured and directed onto a lateral effect position sensing detector such as the PDP90A.

The displacement sensor provides data similar to the pressure sensor. However, displacement is one step closer to the focus from the focusing parabola, and as a result indicates the actual acoustic outcome of the applied ESWL energy. Knowing the distribution of the displacement on the transducer coil outer surface enables modeling of the acoustic focusing that produces a shockwave focus capable of fragmenting kidney stones. Consequently, the displacement sensor is a higher quality measurement of the therapeutic outcome that corresponds to shockwave focusing but informs the therapy model similarly to the current waveform data. At the device and system level, knowing the actual displacement of the transducer completes the measurement of device variables involved in producing a focused shockwave, so diagnostic power now includes the coil performance itself. A variance between expected and actual displacement as a function of input current indicates, for example, fatigue or failure of the coil, or perhaps a loose connection to the transducer.

A Gas Sensor, e.g., ASTI 3TX-DO transmitter, 422 is placed in the water circulation path to enable the measurement of the gas content of the water in the system. At sea level and room ambient temperatures, one expects unpressurized water to have approximately 8 mg/L of gas content. However, lithotripsy commonly prefers 4 mg/L or less for proper operation, and less is better. Consequently, a de-gassing system is used both to remove gas induced by the shockwave cavitation process and to remove gas that is already in the water.

Managing the gas content of the water affects the density of the water, and consequently, the propagation of acoustic waves and their focusing. The effect of the gas for the focusing of acoustic waves is analogous to the effect of fog when focusing optical (electromagnetic) waves: gas introduces blurring of the acoustic wave focusing much like fog does for a human attempting to focus their eyes on a distance object obscured by intervening fog. In much the same way as the effect of fog can be captured mathematically for optical systems using a point spread function or PSF (the distribution of optical energy in a focal plane, or about a focus point), one can represent the effect of gas content to blur or reduce the sharpness of focus for an acoustically focused system by such a PSF function. For the ESWL system, the PSF can be represented by a three dimensional spatial distribution or field and a variable gas level, e.g., PSF(x,y,z,g) where x,y,z describe the width, height and depth of the acoustic focus, with depth being the distance from the focusing element to the stone in the patient body, and g being the gas level. Having characterized the dependence of PSF upon gas level, g, one may adjust PSF at a given time for gas level by adjusting it parametrically, e.g., if modeled as a Gaussian distribution the standard deviation for axes may be altered, or if simply measured directly across diverse gas levels a given gas level may permit substitution of the relevant PSF function. Subsequent to updating the PSF, the size of the focus may be estimated by several means, for example, convolving the PSF with the prior determined system response or by adjusting the nominal system focus response in accord with the derived change in PSF distribution (the two are proportional), etc.

The system used to maintain the gas level uses air and water valves and passive pressures to regulate within a regulation range. However, there is no direct confirmation of the actual gas level, only a gauge-pressure-based extraction of gas that will have as its nominal point whatever the ambient conditions happen to be.

Knowing what the actual levels are opens the possibility of modulating the circulation pump and/or the de-gassing pump operation so as to raise or lower the gas levels in response to a therapy model calculation that uses gas level to compensate for focus spot size, for instance, or energy density (pressure) at the focus, both of which are affected by in-water acoustic scattering or attenuation. The system model uses the gas measurement to help regulate actual gas levels by varying the pump velocity or altering the timing of limit switches and valves. The device model uses the measurements as a means of assessing the health of pumps, the accuracy of calibration and, as a result, the timing of maintenance and/or replacement events, for example.

An Ambient Environment Sensor module, e.g., an embedded Bosch BME280, 424 permits the measurement of the ambient barometric pressure, temperature and relative humidity such that these parameters can be factored into assessments made with other sensor measurements; this sensor also captures the physical orientation, e.g., tilt or rotation, of the system within its environment. Pressure, temperature and humidity are important because shockwave propagation and focusing depend on a set of parameters that includes the air and water temperature, pressure and dissolved gas/vapor content. For the sake of interface (software and electronic) efficiency, this module also includes the capacity to measure device in-system system and specific ambient conditions, most often the device temperature, by including in it the interface electronics for thermistors and thermocouples for lower and higher temperature ranges, respectively. For instance, a thermocouple placed on the Thyratron near its anode enables monitoring of hydrogen gas related tube processes or states, and a thermistor placed on the high voltage and thyratron enclosure can be used to assess the effectiveness of conductive and convective cooling for that subassembly.

This is an integrated sensor that outputs a digital data value for each physical observable or parameter of concern as it is polled by the Data Logger 402. The environmental data is used at the system level for compensating the therapy performance model, as the water system bases its control inputs on an assumption of sea level room ambient or equivalent reference point conditions. This data is used at the device level for compensating control loop parameters, e.g., limit switches and valves, for the known actual temperature, pressure and humidity values. Orientation data are used for assessing the proper level of the system and thus enable an operator alert to be given if excessive incline is detected, for example.

Existing component and/or system models are based on system level failures, usually associated with a component failure (if root cause failure analysis was possible). This enables a probability of failure assessment to be made using data-based probability density functions like the Weibull distribution, e.g., a calculation of mean time between failure and mean time to failure, etc. Using such an approach is better than not using anything, but it leaves open the possibility that a new failure mode exists that was not captured in the prior data, or that a normal but as-yet-unobserved failure mode is present and maturing without the knowledge of the system operator.

An alternative to the exclusive use of a priori statistics is to gather device and system performance data as the system is used so that behavior trends can be observed and performance related indicators are seen well in advance of catastrophic failure. In-process and/or real-time data collection accomplishes this alternative by updating system state knowledge to the time of the procedure or shot within the procedure, which is the most current understanding of the system that one can obtain. The Local Analytics Modeling 440 supports the use of in-process and/or real-time data processing to update an existing therapy or control or maintenance model such that the most recent knowledge of the state of therapy and of the machine used to administer the therapy is used to optimize ongoing patient therapy.

This up-to-date information made available by real-time data collection benefits not only the device and system modeling of performance but also the therapy modeling. This is so because a therapy can be better prescribed if the machine state immediately prior to therapy is known, and is better delivered as therapy advances if the machine state during therapy is known. The therapy model is a function of machine state (pulse energy, acoustic displacement, shockwave focus, environmental conditions, etc.); consequently, having up-to-the-second machine state data enables the delivery of therapies adjusted optimally for the patient and system states at the time of delivery.

Presently there are no in-procedure measurements made of the system and device states, other than the assumed states by virtue of nominal control panel settings. New data available to therapy from the invention include: time series data of voltage, current, pressure, dissolved gas, displacement, along with voltage/current/pressure waveform data for each shot, timing and control data for each shot, and ambient environmental data and machine state data generally. The use of these data inter-procedure and intra-procedure enables a higher maintenance and therapy efficacy by providing feedback to personnel and processes, including computer generated model processes, such that corrective or adaptive changes are made prior to and/or during ESWL therapies.

Feedback and Control

The ESWL system and method includes three levels of control, all aimed at one or two outcomes: therapy efficacy and/or system operational efficacy. Ultimately, even operational efficacy is a matter of therapy efficacy, as more effective operation will produce more effective therapy, regardless of its measurability. The three levels of control addressed here are therapeutic, system and device control.

Therapeutic control is concerned with the selection of operational parameters that are optimum for a particular patient, e.g., such as illustrated in FIG. 12, where a Therapy Optimization Engine and accompanying statistically significant body of data permits the estimation of outcomes as a function of inputs and can also selectively bound inputs or sets of inputs as a function of outcomes. The nominal/minimum/maximum intensity (voltage) and focus of shocks (e.g., set by capacitance value), the duration of the pre-therapy shocks, in-therapy shocks, the rate of shocks over the course of the therapy, the location of the focus with respect to the stone and the manner of accommodating respiration are examples of parameters that can be varied in order to optimize patient care through improved ESWL therapeutic efficacy. Other parameters that are efficacious but are not necessarily therapeutically significant variables include the age (e.g., in shocks) of the therapy components, the type of ESWL technology. Therapeutic control is achieved by means of a therapy model and optimization engine that relies on statistical inference from patient population and historical ESWL data comprised of patient, system and outcome data elements. The invention includes not only static predictive multivariate inference, but also statistical inference approaches that are adaptive, whether the adaptation occurs over the course of one procedure, across multiple patients, or across all patient data and over the course of ESWL history.

Further referring to FIG. 12, there are multiple means of control implied by the directional connectors extending to and from the Therapy Optimization Engine 1200. Outcome data 1206 are not only separated into two classes, they are fed back into the Optimization Engine by updating its model by processing available historical and concurrent system measurements. Patient Characteristics 1202, are observed or collected, e.g., electronic medical records, and input to the Engine so as to select for therapy settings ideal for the patient; conversely, the Engine, given a particular MD or Equipment, etc., may put limits on the allowable or optimal patient characteristics such that a patient may be referred away from ESWL e.g., to a laser therapy, or deferred to another time or setting. Procedural Dependencies 1203, are necessary inputs to the Engine for estimating an expected outcome, and can also be output from an Engine as a set of boundaries for delivering optimal patient care. Equipment Dependencies 1201, likewise, when input to the Engine establish physical boundaries for therapeutic outcomes, but when output as guidance constitute instructions for setting up effective therapy, e.g., by a Tech that is operating the equipment. Tech(nician) Dependencies 1209, reflect the skill and breadth of the Tech capacity to operate the ESWL system and support therapy, and thus are important inputs to include for predicting outcomes; conversely, knowing other system inputs or constraints, the Engine may recommend a particular type of Tech for a therapy to sustain maximum efficacy. MD (medical doctor) Dependencies 1208, like those of the Tech, can drive the quality of care when used as inputs or suggest an alternate caregiver when used as outputs from the Engine. Finally, Stone Parameters 1204, do limit the options for ESWL therapies and, as inputs, enable estimation of efficacy as a function of other inputs, while when used as outputs provide guidance to MD and Tech and Patient concerning advisability of ESWL therapy for that patient.

System control is concerned with attaining and sustaining the system operational state that is required for optimum therapeutic outcomes. Consequently, the system control function involves measuring inputs and outputs of device and system performance and using these measurements to compute corrections to device and system control inputs such that the desired therapeutic control variables are set to the correct and optimum levels.

Device control is concerned with maintaining requisite device behavior such that what's commanded is delivered. This is the narrowest scope of control in the system, typically, and ranges from, for example, the local control of pump velocity to the stabilization of the high voltage supply output at a control point needed for a particular shock energy level.

Both system and device control support a secondary, but nonetheless important role for the collection of data for control: predictive maintenance. Having the system be assuredly available for a procedure is vitally important to achieving efficacy, though system availability is a more binary input to efficacy than, for instance, water pump pressure. The collection of data on device and system outputs over time enables the statistical inference of device and, consequently, system, probabilities of continued operation and/or failure. Computing these probabilities based on device physical models and also system and device historical failure data leads to predictive power for failures. Knowing when failure is likely enables timely maintenance and parts scheduling such that uninterrupted service to patients can be provided. Combining the therapy prediction with maintenance prediction allows a joint optimum for sustained optimal patient care over time. For example, if there was a statistically significant probability of equipment failure during a procedure, such that a suboptimal result could occur when components were repaired, the procedure might be rescheduled or maintenance might be accelerated or equipment settings might be tested (using a Therapy Optimization Engine such as portrayed in FIG. 12) and used to form a strategy for handling an equipment breakdown that sustained a low Complication rate, for example.

The following paragraphs narrate the concepts captured in the several figures/diagrams that illustrate the control elements.

Figure 5:
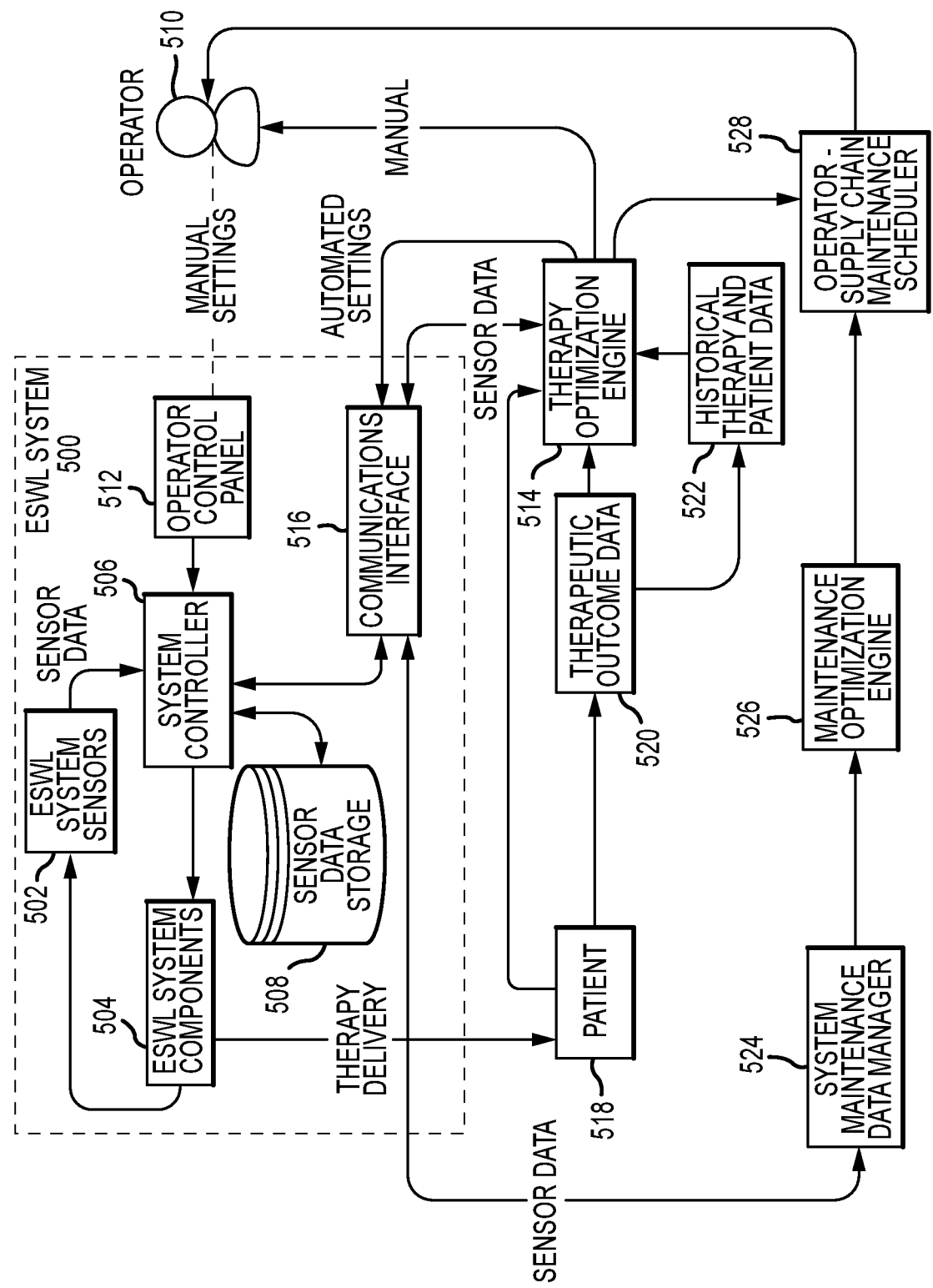
FIG. 5 is a block diagram illustrating an embodiment of system level control of the ESWL system.

As depicted in FIG. 5, System Level Control focuses on two levels of control: therapy and system. Device level control is implied. The diagram also captures two types of efficacy: therapeutic and operational. Included in the operational efficacy is the role of predictive maintenance in sustaining operational efficacy.

The largest single functional block is an ESWL System 500, containing the suite of ESWL System Sensors 502 that derive data from the ESWL System Components 504, which are, in turn controlled/commanded by a System Controller 506. The sensor data is used for control but also analysis and diagnostics, so there is local Sensor Data Storage 508 in the ESWL System to support these tasks. Presently all major control parameters are set by an operator 510. An Operator Control Panel 512 supplies those parameter values by means of Operator input. However, a computerized Therapy Optimization Engine 514, such as is presently used to inform the operator, may be used to automatically command the System Controller and assure that efficacious performance is achieved with the ESWL System (FIG. 12 is a possible structure for a Therapy Optimization Engine). In the case of automated parameter setting, a Communications Interface 516 enables the parameters to be communicated to the ESWL System and used by its System Controller.

Inside the ESWL System block the control loop running amongst the System Controller, ESWL System Components and ESWL System Sensors accomplishes the system control function. The remaining elements of the diagram are present primarily to support therapeutic and operational efficacy objectives.

The therapy control shown in the diagram occurs at two levels: intra-procedure and inter-procedure. Intra-procedural control begins with the delivery of therapy to that Patient 518 so as to produce Therapeutic Outcome Data 520, e.g., intra-procedure this includes operator observations of stone fragmentation or similar data by automated image processing means from patient urological sonar or X-ray imagery. This Outcome Data is input to the Therapy Optimization Engine that leverages a representation of Historical Therapy and Patient Data 522, plus the current (up-to-the-shot) Sensor Data, all informed by the Patient Data. The Optimization Engine is then able to update the estimate of the optimal therapy parameters. The results can be communicated to the System Controller in real time for direct control of the ESWL System or they can be provided to the Operator and entered manually.

Inter-procedural control is accomplished similarly to intra-procedural control. However, whereas the intra-procedural control is usually constrained by time and computing resources to use a representation of the Historical Therapy and Patient Data, the inter-procedural control may have enough time and resources to recomputed solutions using more granular data. Also, the inter-procedural control will have the benefit of knowing the final Therapeutic Outcome Data rather than interim data that is necessarily preliminary. The inter-procedural control also has the advantage of resources such that offsite computing (e.g., so called cloud computing) may be used to gain the perspective that spans multiple procedures, geographies, cultures, ESWL Systems and system types or brands—a global or more universal perspective of optimality.

The implication and clear intention of the Therapy Optimization Engine and its continuous incorporation of therapy-related data is so-called "machine learning". The arrival of new information from procedures taking place at different times and different locations serves to "instruct" the Optimization Engine as to what is optimal for the next patient and next procedure, with the understanding that optimality will change as the estimation power of the Engine improves by virtue of greater depth and breadth of data. This applies both to the therapy and the ESWL system and individual device operating parameters to provide the therapy.

The final control element shown on this diagram is that of operational control by way of optimum maintenance. Using the Communication Interface to obtain sensor data from Sensor Data Storage, a System Maintenance Data Manager 524 inputs data into a Maintenance Optimization Engine 526 e.g., based on an API or local executable such as Weibell++ or Synthesis API (Reliasys Corporation), that informs the Operator-Supply-Chain Maintenance Scheduler 528. The Scheduler has access to the data repository containing the Therapy Optimization Engine outputs and so is able to account for variations of required therapy that would mandate a component change sooner rather than later, or any temporal-performance combination that may occur. Consequently, for example, if patient and system inputs are used to compute recommended starting points for a therapy and there is an optimum available that is enabled by a new pump, for example, the Maintenance Scheduler would notify an operator or technician of the need for maintenance and enable the higher efficacy procedure to take place by virtue of optimal hardware configuration.

In all of these control regimes, the sensor data is instrumental in enabling efficacy. Present ESWL systems do not record and make available the sensor data needed for the controls implied by the System Level Control diagram. Data are partially available based on bi-annual maintenance, but only for high voltage settings and capacitance levels (in other cases, valves and switches are verified for operation at nominal set points). The invention enables data collection during procedures, for every shot, at critical performance points, in sufficient resolution and accuracy to support efficacy modeling at the therapeutic levels. The data are more accurate, more granular. Models of therapy benefit by knowing the actual (rather than presumed) behavior of the system, by knowing the statistical variation of system variables, and by knowing the inter-system and inter-procedure variations that accompany the distinct outcome and patient data for each procedure. The result is that phenomena presently regarded as spurious are given a basis in data-fact such that the error of prediction is reduced and the ability to drive efficacy increased by way of lower noise in model inputs and higher correlation between inputs and outputs.

Figure 6:
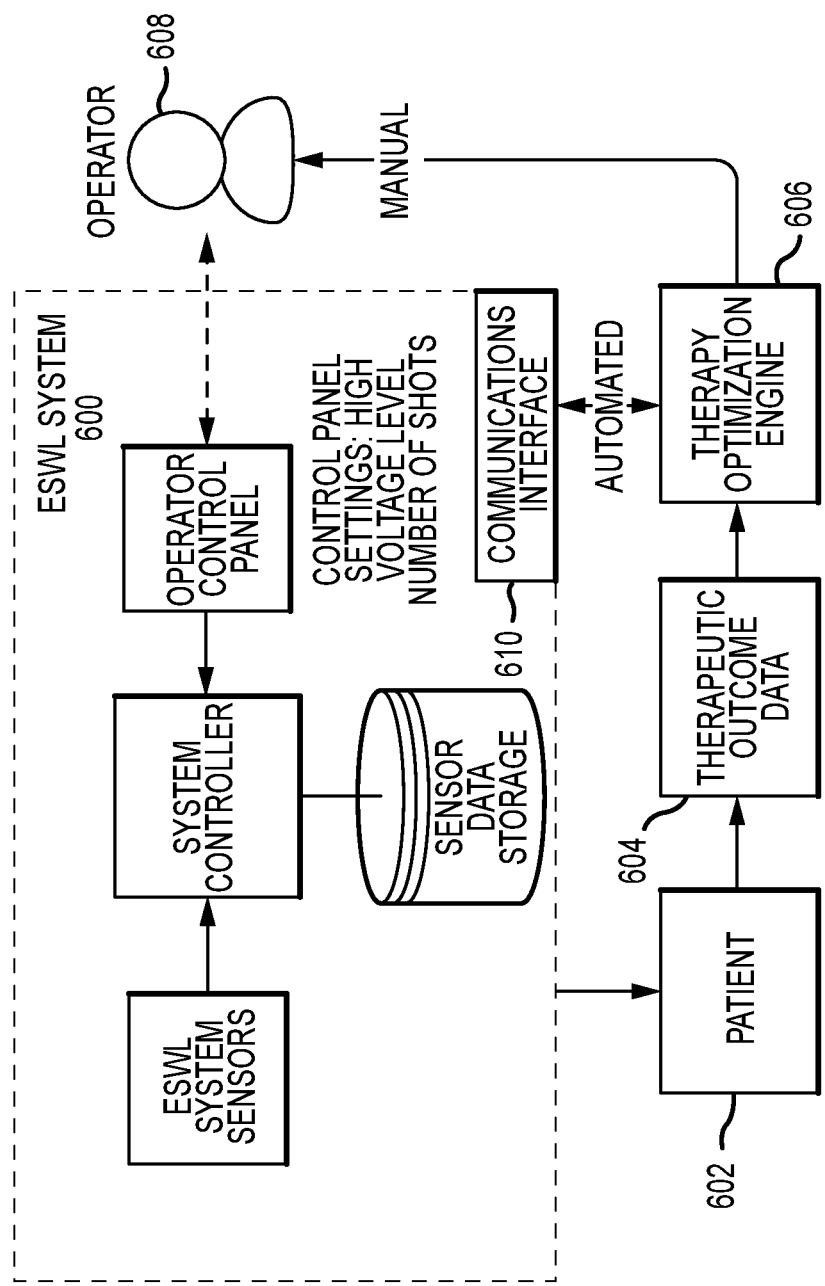
FIG. 6 is a block diagram illustrating an embodiment of a system sensor operator loop.

A System Sensor Operator Loop depicted in FIG. 6 communicates the therapeutic control of the ESWL system based on sensor data. It is implicit in this diagram that a model for therapy optimization is used such that sensor and patient data can be incrementally used to optimize therapy settings (see discussion on system level control). The operation begins with an ESWL System 600 that operates on a Patient 602 and generates interim Therapeutic Outcome Data 604 such that a Therapy Optimization Engine 606 can compute optimal settings for therapy. These settings can then be introduced into the therapy by an Operator 608 (manually) or by the ESWL System internally through its Communication Interface 610. The sensor data supplies the model with actual device and system data rather than presumed data.

The following diagrams illustrate device level control of certain exemplary components of the ESWL system.

Figure 7A:
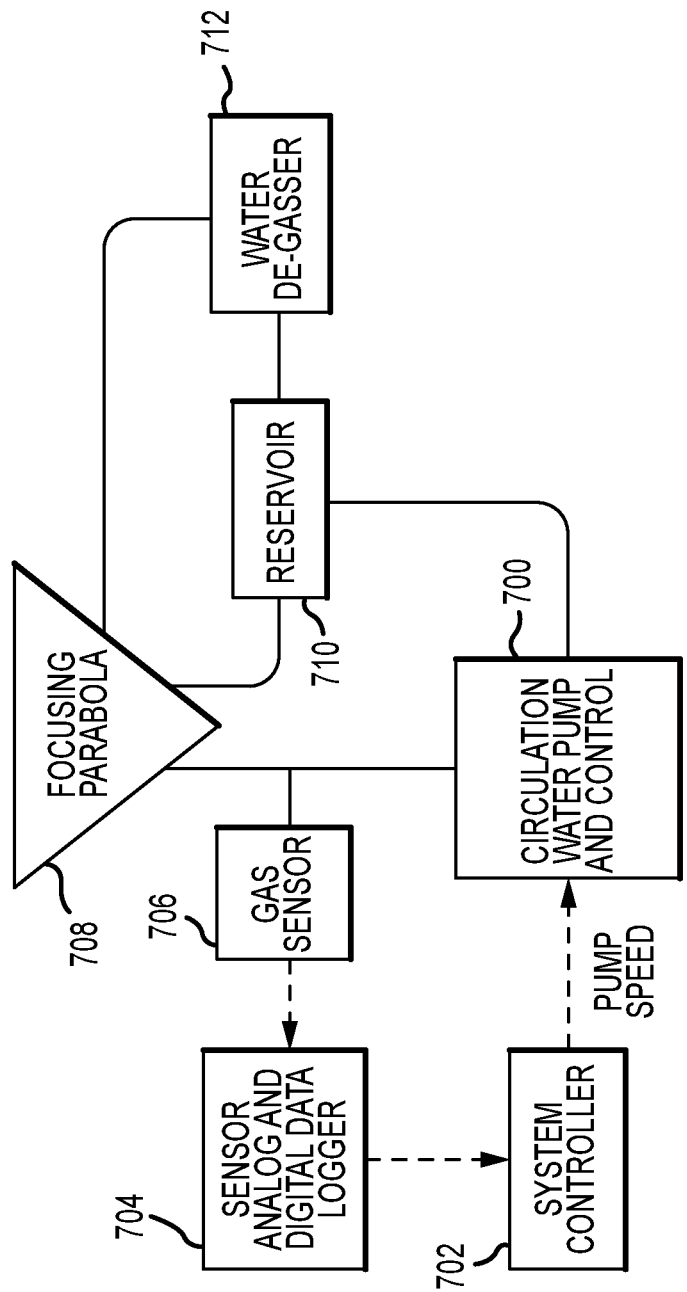
FIGS. 7a-7d are block diagrams illustrating embodiments for De Gas Loop, displacement and bowl pressure loop, heater-light-detect loop and voltage-current loop control.

A De Gas Loop in FIG. 7a illustrates the control of pump speed in a Circulation Water Pump and Control module 700 as commanded by a System Controller 702 informed by a Sensor Analog and Digital Data Logger 704. The Logger obtains its information from a Gas Sensor 706 that provides digital data related to the gas content of the water re-entering the Pump from a Focusing Parabola 708. The Parabola has water inlets and outlets at its base, connected to a Pump and Reservoir 710. Near the top of the Parabola is a siphon mechanism to capture gaseous water from the Parabola, the gas content being boosted by the action of the shockwaves producing cavitation. This water is passed through a Water DeGasser 712 where a pressure differential is exploited to force gas out of the water before recirculating it via the Reservoir.

Figure 7B:
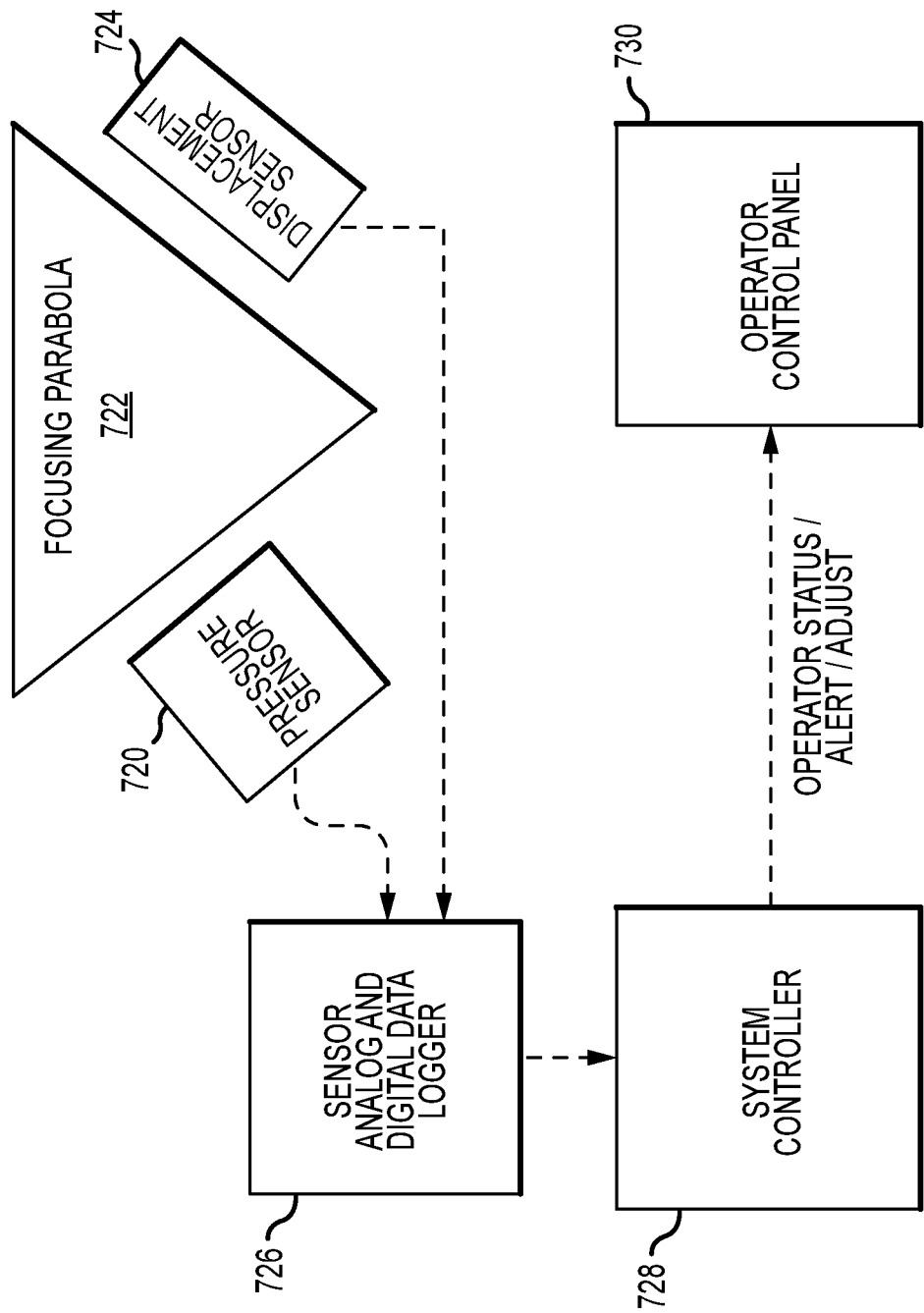

A Displacement and Bowl Pressure Loop in FIG. 7b illustrates the capture of both Pressure Sensor 720 (1 or more sensors) from the side wall of the (often brass) Focusing Parabola 722 and the Displacement Sensor 724 having a field of view through the Parabola and onto the acoustic transducer contained within it (not shown, see FIG. 4). The Logger 726 captures these data elements and feeds them to the System Controller 728 such that an operator alert can be communicated by way of the Operator Control Panel 730. Though it is not shown, an understanding of the system control diagram implies the inclusion of automated control in the ESWL System and the use of these data by computerized means.

Figure 7C:
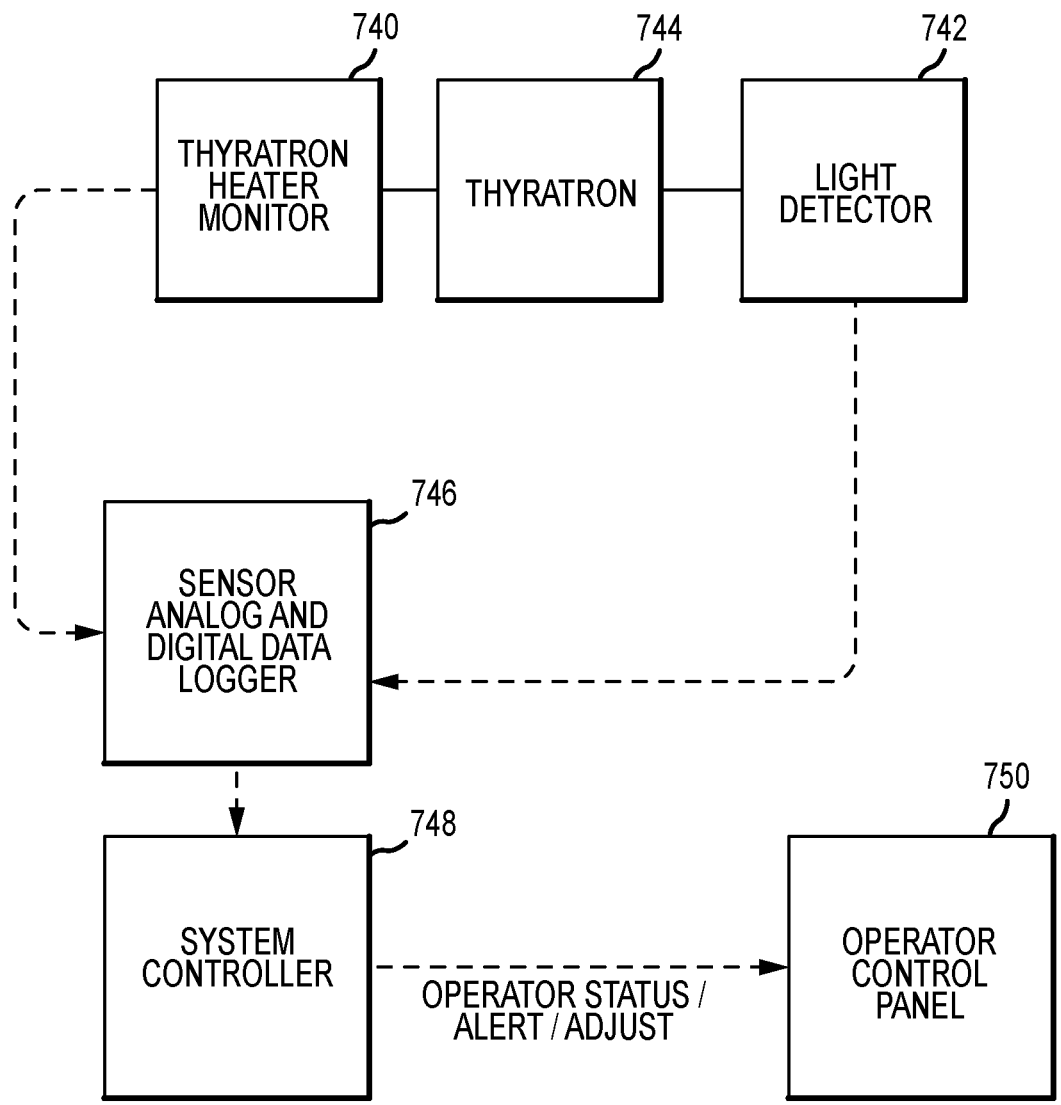

A Heater-Light-Detect Loop in FIG. 7c illustrates the capture of data from a Thyratron Heater Monitor 740 and a Light Detector 742 positioned about a Thyratron 744, used for maintaining optimal plasma levels for shockwave production and for verifying the occurrence of a thyratron event, respectively. This is an alternate or supplement to using the thyratron heater voltage derived from measurements in the Thyratron Heater Monitor. The Sensor Analog and Digital Data Logger 746 allows these data to be communicated to the System Controller 748, which in accordance with the system control diagram can use the data for computerized control functions or, as shown here, instruct an operator by means of the Operator Control Panel 750.

Figure 7D:
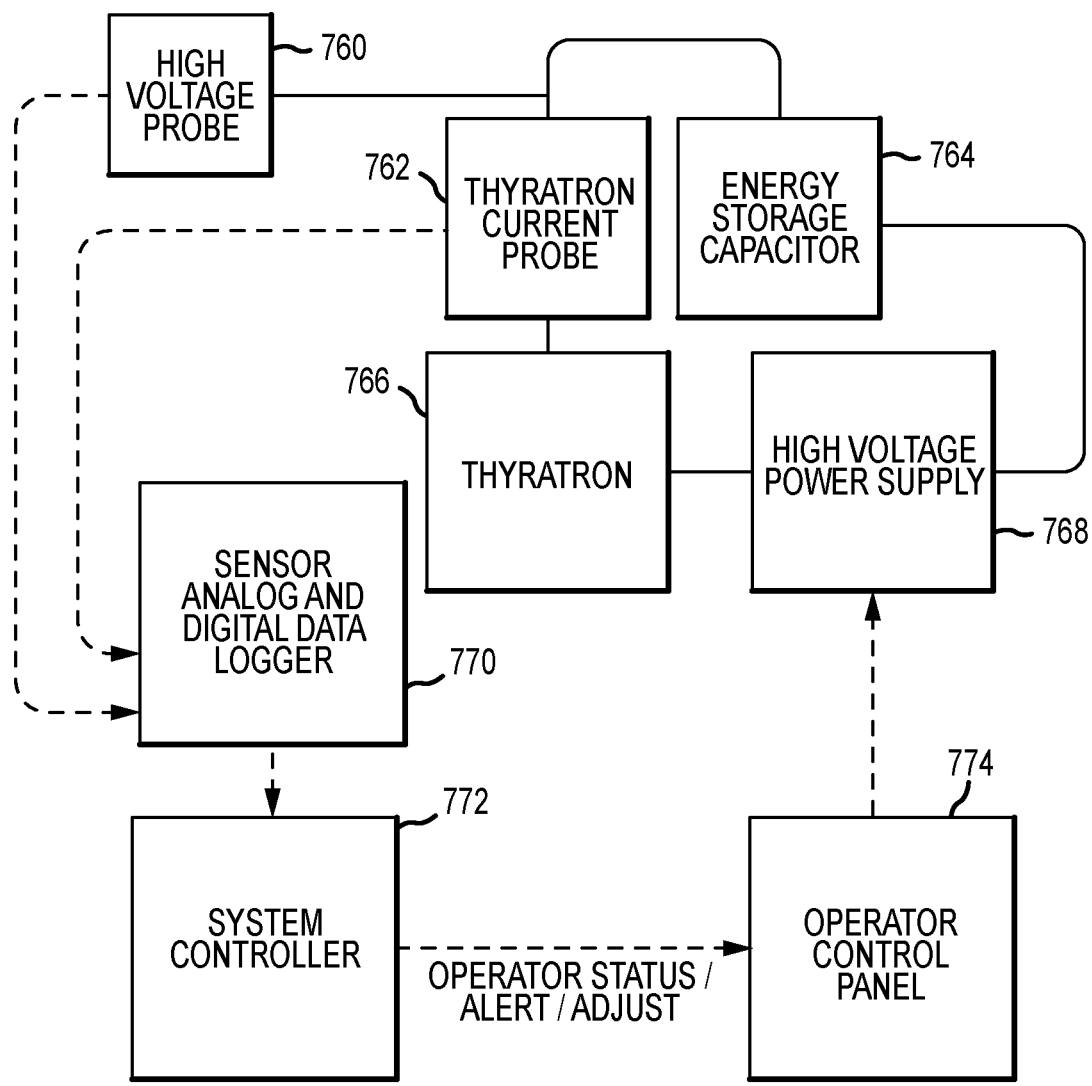

A Voltage-Current Loop in FIG. 7d shows how the data from High Voltage Probe 760 and Thyratron Current Probe 762 modules are measured at an Energy Storage Capacitor 764 and Thyratron 766, respectively (the Current Probe makes its measurement by encircling the conductor between the Capacitor and the Thyratron). The voltage present is identical to the voltage on the High Voltage Power Supply 768, the two being connected by a low resistance conductor. The voltage and current thus measured are input to the Sensor Analog and Digital Data Logger 770 such that the System Controller 772 can use the data for automated system control and optimization functions or, as shown here, control of optimality through messages and instructions communicated to an operator through the Operator Control Panel 774.

Figure 8:
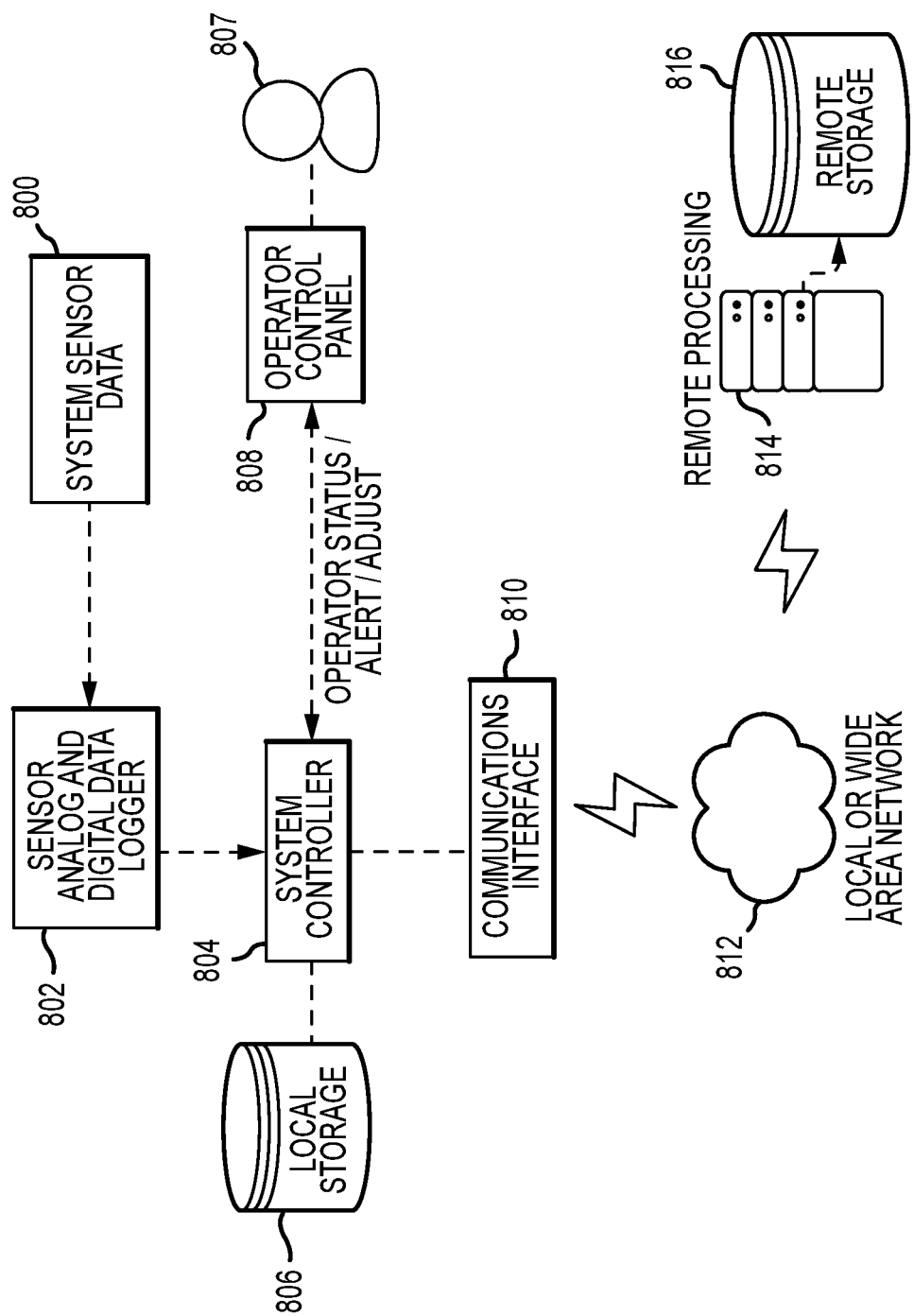
FIG. 8 is a block diagram illustrating an embodiment of a store-process loop.

A Store-Process Loop in FIG. 8 illustrates the facility of the invention for managing both local (in the ESWL System) data storage, e.g., nonvolatile memory storage, or remote storage, e.g., cloud data services. System Sensor Data 800 are collected through the Sensor Analog and Digital Data Logger 802 and prepared for storage (formatted, aggregated) by the System Controller 804 (if not already so prepared by the Logger) and written to Local Storage 806 assets in the system. These data are viewable and/or in some cases editable by an operator 807 by means of the Operator Control Panel 808. These data are also transmissible to remote data stores via a Communication Interface 810 that accesses a Local or Wide Area Network 812 to which are connect Remote Processing 814 compute resources and their associated Remote Storage 816 facilities.

Figure 9:
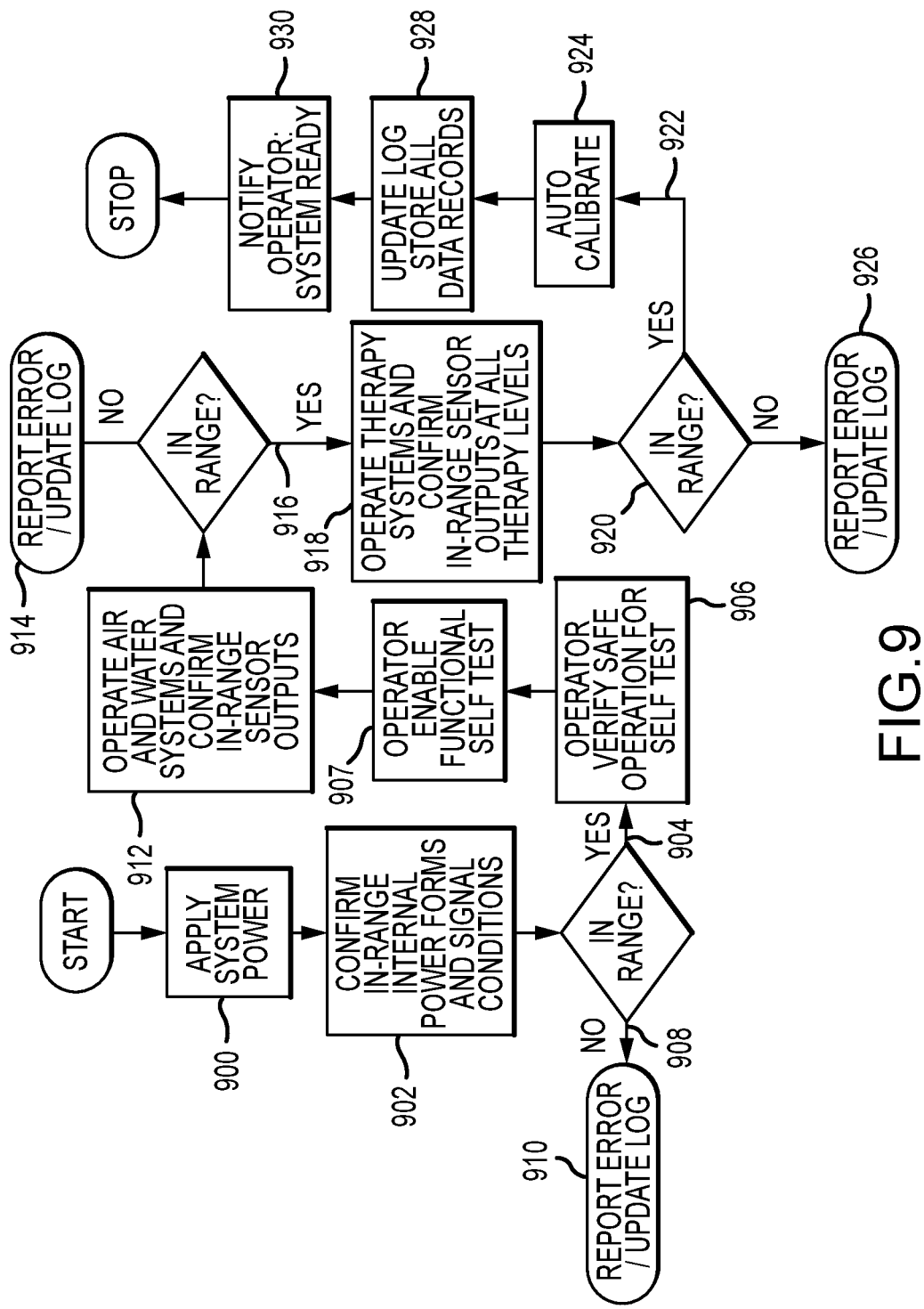
FIG. 9 is a flow diagram of an embodiment of power on self test (POST), auto calibrate.

A Power-On Self-Test and Auto Calibrate are illustrated in FIG. 9. The logical flow of events to support power on self-test (POST) and subsequent self or auto-calibration is described in this figure. The process begins with the action to Apply System Power 900, after which time the system controller samples the internal power supply monitors to Confirm In-Range Internal Power Forms and Signal Conditions 902. Here, the state of being "In-Range" means that the values measured are within the range that can be accommodated by system operation and also that can be adjusted or compensated for by way of calibration. Also, it is assumed that there is some periodic calibration of the system calibrators themselves, so as to avoid drift in system values.

If Internal Forms are in range 904, the system is ready for the Operator to Verify Safe Operation 906 and Enable Functional Self-Test 907. If not 908, an error is reported to the operator and a log of system measurements and status is updated 910. An in-range confirmation advances the state to the action Operate Air and Water Systems and Confirm In-Range Sensor Outputs 912; an out of range result produces an error condition and halts progress 914. An in-range result 916 enables the onset of the action to Operate Therapy Systems and Confirm In-Range Sensor Outputs at All Therapy Levels 918 such that the full range of the system therapeutic capability is exercised and measured 920.

When the therapeutic range of operation has been explored and found to be in range of useful manipulation 922, the auto calibration 924 can proceed. Otherwise, an error is generated and data are logged as before 926. When the Auto Calibrate action is taken, the measurements of system behavior as a function of system control inputs are used to generate functions for control such that the system control is maximally informed of any drift in performance. This is akin to a curve fit of measured data such that, thereafter, the fitted function establishes a norm for prediction and control.

At the completion of calibration, the actions to Update Log, Store All Data Records 928 can be taken prior to the operator notification and System Ready state 930, which concludes this test and calibrate function. It is expected that calibration will be performed routinely at system start as part of maximizing efficacy; however, the design also contemplates and provisions a continuous auto-calibrate where by the device and system outcomes are monitored and adjusted as therapies proceed, so that maximum efficacy is not only established at the outset of therapy, but is sustained throughout a therapy.

Figure 10:
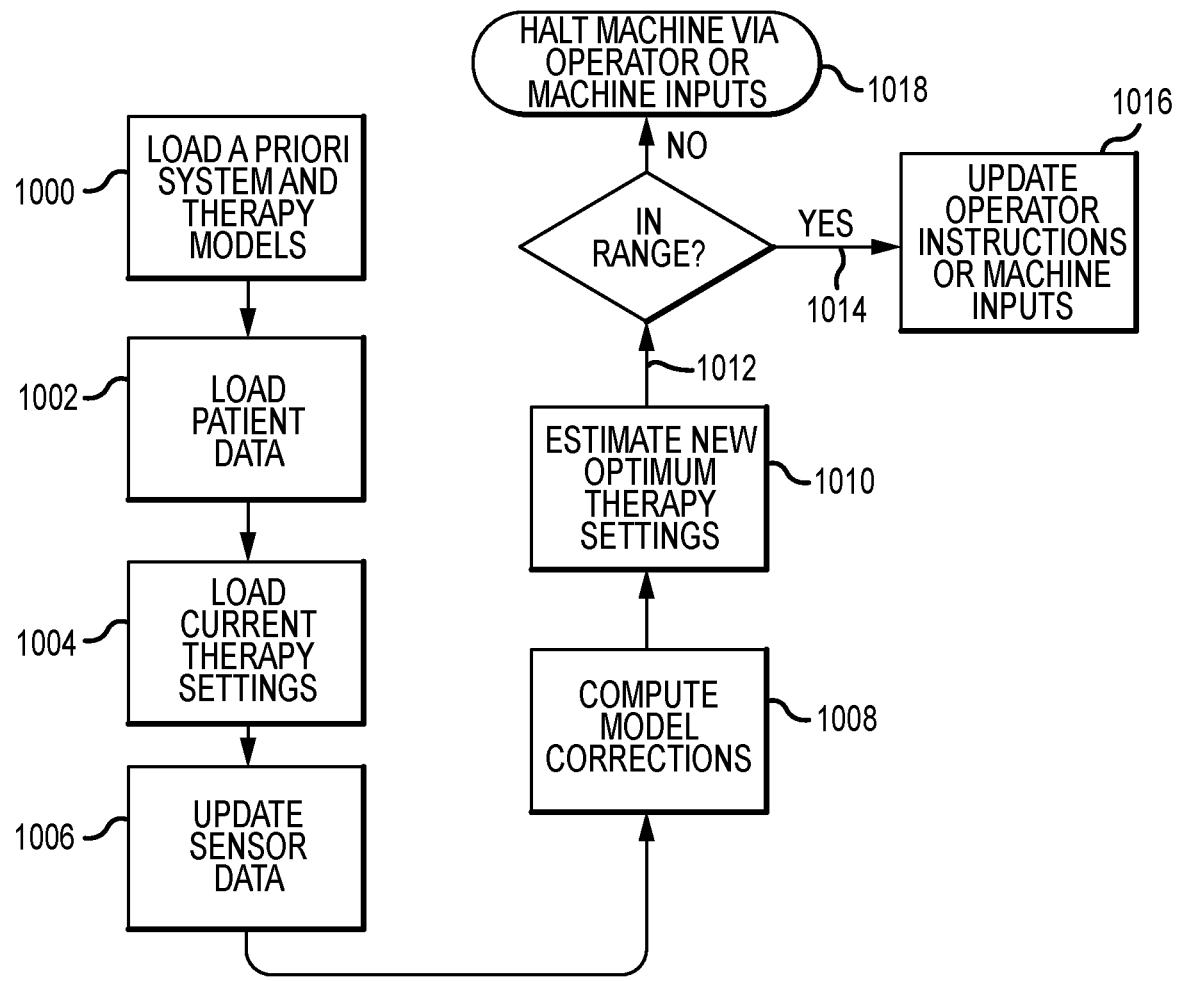
FIG. 10 is a flow diagram of an embodiment of therapy optimization engine with forced off condition.

A Therapy Optimization Engine with Forced Off Condition in FIG. 10 details some of the operations underlying the Therapy Optimization Engine called out in prior figures, e.g., system control, and also introduces an implied function of the system control, namely, the imposition of a Forced Off in the event of an unrealizable control scenario. The process begins by the action to Load A Priori System and Therapy Models 1000 and proceeds to Load Patient Data 1002 after which step the controller can Load Current Therapy Settings 1004 and then conclude the data grabbing exercise with an Update Sensor Data 1006 step. Given the presence of new information from the patient and the system, e.g., its sensor data, the processor employed can Compute Model Predictions 1008 based on this new information and then use the updated model to Estimate New Optimum Therapy Settings 1010. The new optimum can be computed based only on locally available data if computing resources and time are scarce; however, in general, the optimization of therapy settings takes place in view of historical patient/therapy/device data spanning ESWL technologies, geographies and epochs—in short, all ESWL data available to the Engine at the time of computation. Since it is possible to compute values that are not appropriate, optimum or perhaps even realizable, the range of settings is evaluated 1012. If they are IN RANGE 1014 then the ESWL System can be updated manually or automatically prior to beginning or continuing the ESWL therapy 1016. If the settings are not IN RANGE then the machine is halted automatically or through operator intervention (this is the Forced Off condition) 1018.

Figure 2:
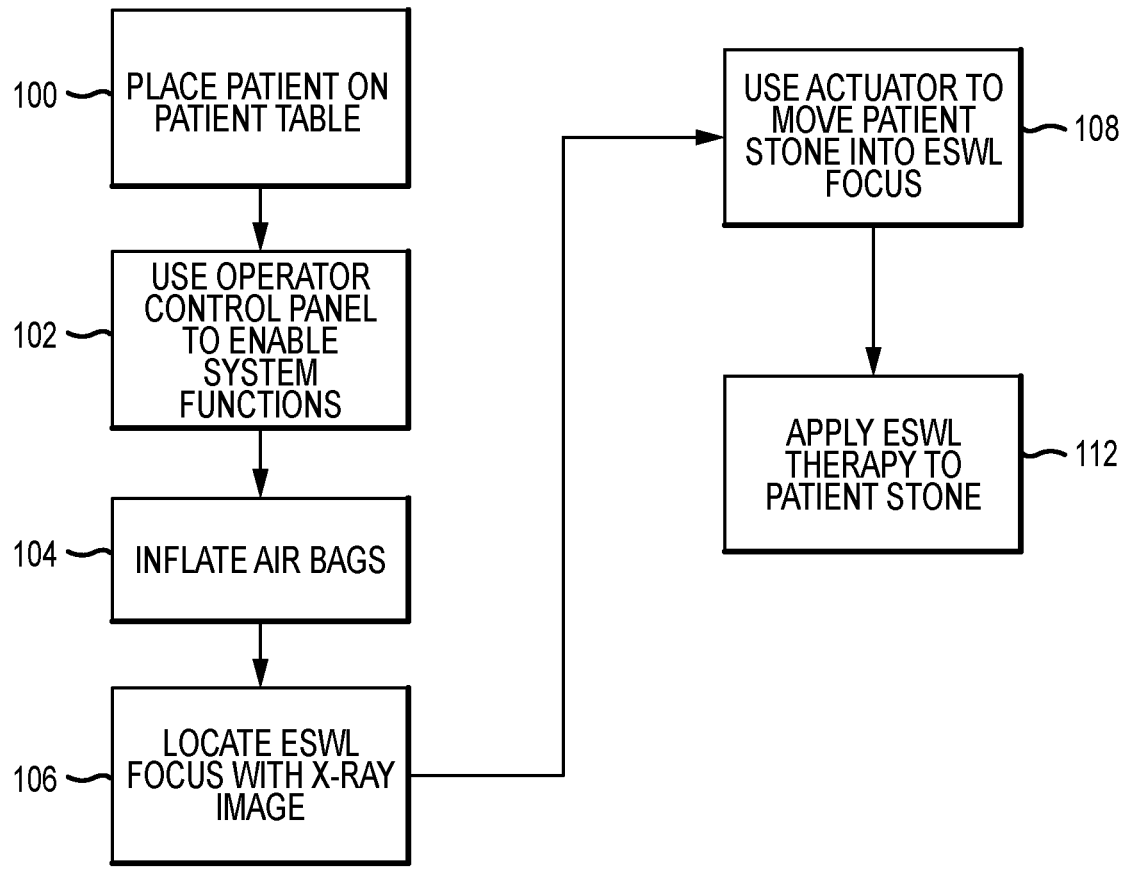
FIG. 2, as described above, is a flow diagram for providing kidney stone therapy to a patient using the ESWL system.
Figure 3:
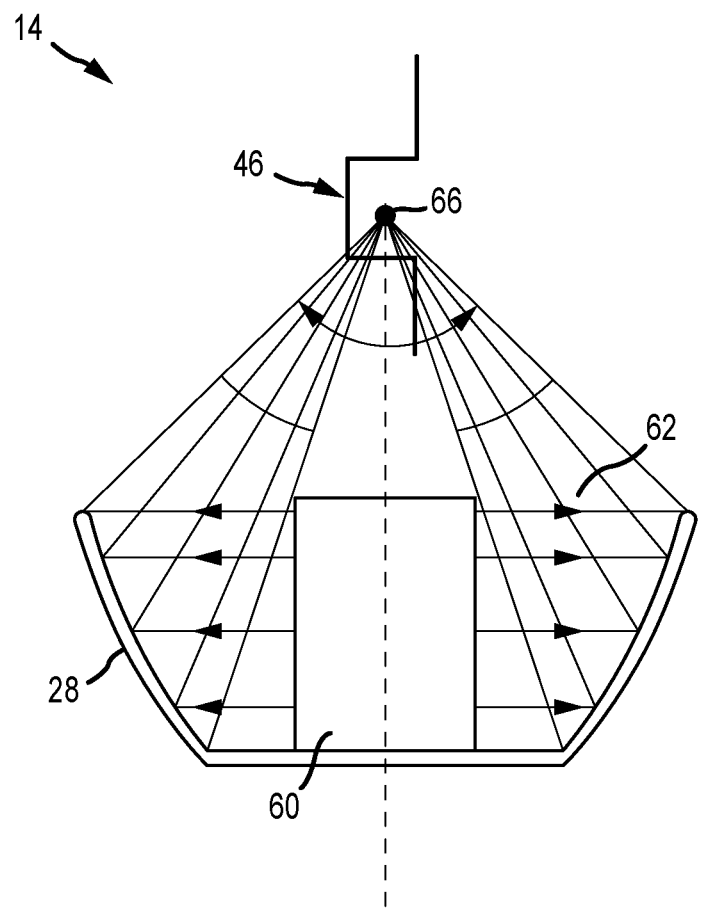
FIG. 3, as described above, is a diagram of an acoustic transducer.
Figure 11:
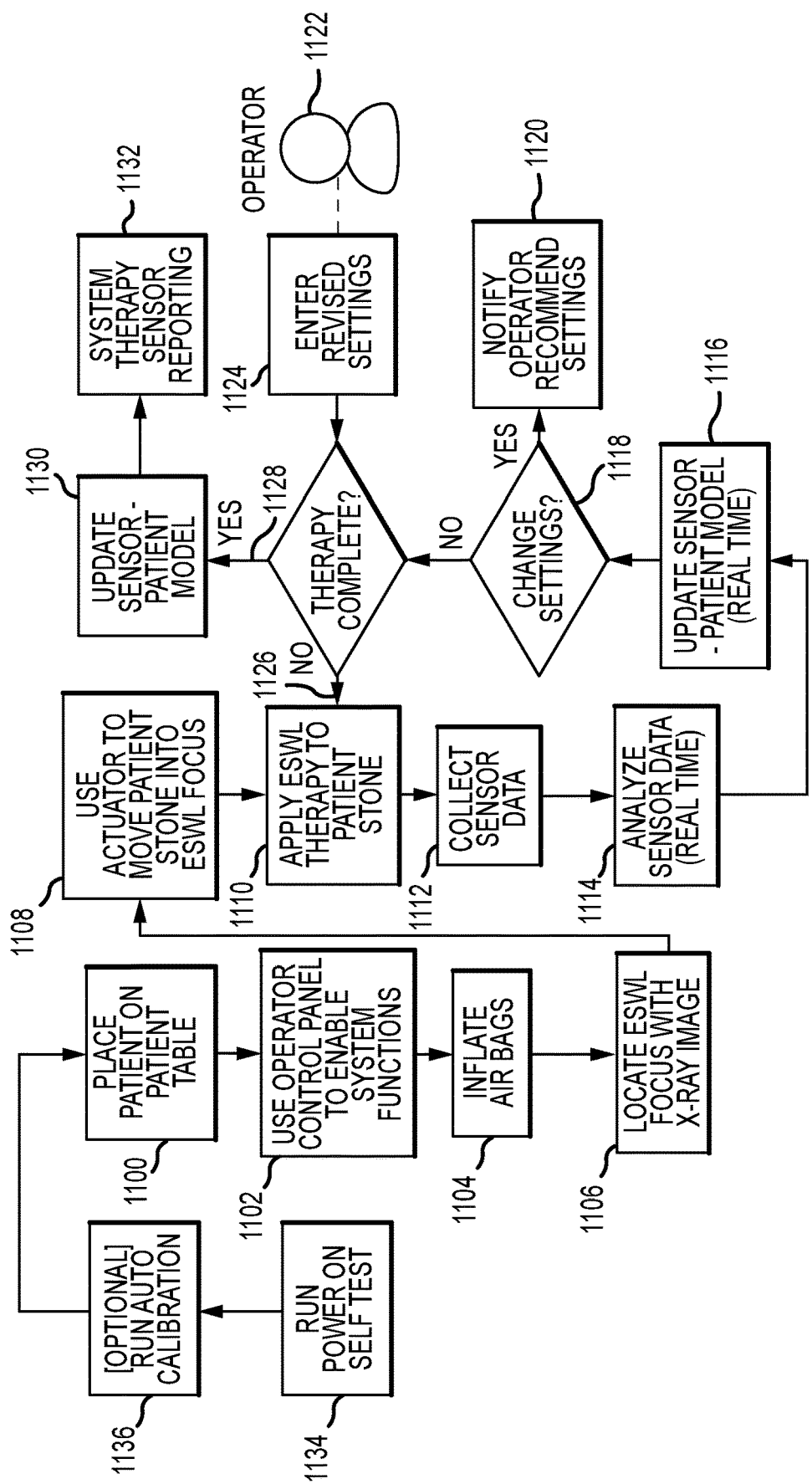
FIG. 11 is a flow diagram for providing kidney stone therapy to a patient using the ESWL system with device and system data sensed in-situ and therapy/system/device control.

A flow diagram FIG. 11 of an ESWL system and method including in-situ sensing and control depicts some of the flow innovation of the invention over the prior art as illustrated in FIG. 2. The significant additions captured in this aspect of the invention are the collection of data, modeling of sensor/system models, and the incorporation of therapy models coupled to sensor/system models for therapy optimization (also articulated in system model Figure).

As before, a patient is placed on a patient table 1100. An operator uses an operator control panel to enable system functions 1102 to inflate air bags 1104, locate ESWL focus with an X ray image 1106, use an actuator to move the patient stone into ESWL focus 1108 and apply the ESWL therapy to the patient stone 1110.

Accordingly, whereas the prior art flow of events starts by placing a patient on the table and comes to a conclusion after Apply ESWL Therapy to Patient Stone 1110, the invention begins with a system Power On Self-Test 1134 and allows for a (nominally advised) Auto Calibration 1136 before continuing after 1110, from which it proceeds to Collect Sensor Data 1112 and then use this data to Analyze Sensor Data 1114 and subsequently Update Sensor-Patient Model 1116, both in real time when one is intra-procedure. Given an updated model, if the update suggests a need to change the parameters for the procedure the assessment to Change Settings 1118 can be made, after which time the system will Notify Operator and Recommend Settings 1120 from which the Operator 1122 will Enter Revised Settings 1124 and therapy can continue if it is not then complete 1126 (usually indicated by expiration of a shot counter or an assessment of successful fragmentation). When therapy is completed 1128 the system and sensor data state at the conclusion of the procedure are used to Update Sensor-Patient Model 1130 and then produce an output usable by other systems and subsequent procedures by way of the System Therapy Sensor Reporting 1132 activity.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. A system for enhancing efficacy for therapeutic or operational outcomes of an extracorporeal shockwave lithotripsy (ESWL) patient therapy, comprising:
   an ESWL system including a plurality of hardware devices configured to produce a focused acoustic shockwave coincident with a patient's kidney stone, wherein the hardware devices comprise an electrical power source configured to charge an energy storage element to provide current to drive an electronically controlled current switch that supplies a high current pulse to an acoustic transducer to originate an acoustic wave for a focusing element, which in turn generates the focused acoustic shockwave, and a water circulation system configured to circulate and degas water to assure acoustic propagation and focus;
   one or more sensors embedded in-situ with said hardware devices, said sensors configured to sense data including operating parameters and outputs of a plurality of the hardware devices, wherein the one or more sensors includes a voltage probe to measure a discharge waveform from the energy storage element for the shockwave, a current probe configured to measure a switch current passing from the switch into the acoustic transducer, one or more pressure sensors proximate to the focusing element to measure a pressure gradient produced by the shockwave and a gas sensor in the water circulation path to measure the gas content of the water;

a system sensor data acquisition and storage assembly configured to capture data from the sensors during operation of the ESWL system to produce the focused acoustic shockwave; and one or more computer processors configured to process the discharge waveform, the switch current and the pressure gradient to estimate a pressure applied to the patient kidney stone and to process the gas content of the water to estimate a focus of the acoustic shockwave to provide feedback to control the ESWL system.

2. A system for enhancing efficacy for therapeutic or operational outcomes of an extracorporeal shockwave lithotripsy (ESWL) patient therapy, comprising:

an ESWL system including a plurality of hardware devices configured to produce a focused acoustic shockwave coincident with a patient's kidney stone, wherein the hardware devices comprise an electrical power source configured to charge an energy storage element to provide current to drive a thyratron tube that supplies a high current pulse to an acoustic transducer to originate an acoustic wave inside a focusing element, which in turn generates the focused acoustic shockwave, and an adjustable external AC power supply or an adjustable internal thyratron voltage transformer;

one or more sensors embedded in-situ with said hardware devices, said sensors configured to sense data including operating parameters and outputs of a plurality of the hardware devices, wherein the one or more sensors include a thyratron heater monitor to measure a thyratron heater voltage and current;

a system sensor data acquisition and storage assembly configured to capture data from the sensors during operation of the ESWL system to produce the focused acoustic shockwave; and one or more computer processors configured to process the data to compare the estimated thyratron heater voltage and current to specified values and adjust the external AC power supply or internal thyratron voltage transformer to control the thyratron heater voltage and current to the specified values to provide feedback to control the ESWL system.

3. A system for enhancing efficacy for therapeutic or operational outcomes of an extracorporeal shockwave lithotripsy (ESWL) patient therapy, comprising:

an ESWL system including a plurality of hardware devices configured to produce a focused acoustic shockwave coincident with a patient's kidney stone, wherein the hardware devices comprise an electrical power source configured to charge an energy storage element to provide current to drive a thyratron tube that supplies a high current pulse to an acoustic transducer to originate an acoustic wave for a focusing element, which in turn generates the focused acoustic shockwave;

one or more sensors embedded in-situ with said hardware devices, said sensors configured to sense data including operating parameters and outputs of a plurality of the devices, wherein the one or more sensors include a light detector to measured light emitted from the energized thyratron tube charge plasma;

a system sensor data acquisition and storage assembly configured to capture data from the sensors during operation of the ESWL system to produce the focused acoustic shockwave; and one or more computer processors configured to process the measured light to estimate a present state and statistical behavior of the thyratron tube concerning intensity and spectral content, and assess the thyratron tube's health to adjust a maintenance schedule or a patient therapy to provide feedback to control the ESWL system.

* * * * *